US011896432B2

(12) United States Patent
Villongco et al.

(10) Patent No.: US 11,896,432 B2
(45) Date of Patent: Feb. 13, 2024

(54) MACHINE LEARNING FOR IDENTIFYING CHARACTERISTICS OF A REENTRANT CIRCUIT

(71) Applicant: Vektor Medical, Inc., Carlsbad, CA (US)

(72) Inventors: Christopher J. T. Villongco, Roswell, GA (US); Adam R. Geronemus, Miami, FL (US); Robert Joseph Krummen, Bellevue, WA (US)

(73) Assignee: Vektor Medical, Inc.

( * ) Notice: Subject to any disclaimer, the term of this patent is extended or adjusted under 35 U.S.C. 154(b) by 0 days.

(21) Appl. No.: 18/358,922

(22) Filed: Jul. 25, 2023

(65) Prior Publication Data

US 2023/0380809 A1 Nov. 30, 2023

Related U.S. Application Data

(63) Continuation of application No. PCT/US2022/039627, filed on Aug. 5, 2022, and a
(Continued)

(51) Int. Cl.
*A61B 5/055* (2006.01)
*A61B 8/08* (2006.01)
*A61B 6/03* (2006.01)

(52) U.S. Cl.
CPC .............. *A61B 8/483* (2013.01); *A61B 5/055* (2013.01); *A61B 6/032* (2013.01); *G06T 2207/30048* (2013.01)

(58) Field of Classification Search
CPC .................................................... A61B 8/483
See application file for complete search history.

(56) References Cited

U.S. PATENT DOCUMENTS

| 4,352,163 A | 9/1982 | Schultz et al. |
| 5,458,116 A | 10/1995 | Egler |

(Continued)

FOREIGN PATENT DOCUMENTS

| CN | 105263405 A | 1/2016 |
| CN | 106725428 | 5/2017 |

(Continued)

OTHER PUBLICATIONS

Acharya et al., A deep convolutional neural network model to classify heartbeats, Computers in Biology and Medicine (Oct. 1, 2017) vol. 89, pp. 389-396.

(Continued)

*Primary Examiner* — Oneal R Mistry
(74) *Attorney, Agent, or Firm* — Perkins Coie LLP

(57) ABSTRACT

A system is provided for augmenting a three-dimensional (3D) model of a heart to indicate the tissue state. The system accesses a 3D model of a heart, accesses two-dimensional (2D) images of tissue state slices of the heart, and accesses source location information of an arrhythmia. The system augments the 3D model with an indication of a source location based on the source location information. For each of a plurality of the tissue state slices of the heart, the system augments a 3D model slice of the 3D model that corresponds to that tissue state slice with an indication of the tissue state of the heart represented by the tissue state information of that tissue state slice. The system then displays a representation of the 3D model that indicates the source location of the arrhythmia and the tissue state of the heart.

24 Claims, 15 Drawing Sheets

Related U.S. Application Data continuation of application No. 17/882,426, filed on Aug. 5, 2022.

(60) Provisional application No. 63/231,022, filed on Aug. 9, 2021.

(56) References Cited

U.S. PATENT DOCUMENTS

| | | |
|---|---|---|
| 5,596,634 A | 1/1997 | Fernandez et al. |
| 5,601,084 A | 2/1997 | Sheehan |
| 5,803,084 A | 9/1998 | Olson |
| 5,891,132 A | 4/1999 | Hohla |
| 6,269,336 B1 | 7/2001 | Ladd et al. |
| 6,292,783 B1 | 9/2001 | Rohler et al. |
| 6,324,513 B1 | 11/2001 | Nagai et al. |
| 6,370,412 B1 | 4/2002 | Armoundas et al. |
| 6,567,805 B1 | 5/2003 | Johnson et al. |
| 6,895,084 B1 | 5/2005 | Saylor et al. |
| 6,931,273 B2 | 8/2005 | Groenewegen et al. |
| 7,010,347 B2 | 3/2006 | Schecter |
| 7,286,866 B2 | 10/2007 | Okerlund et al. |
| 7,424,137 B2 | 9/2008 | Badilini et al. |
| 8,224,640 B2 | 7/2012 | Sharma et al. |
| 8,521,266 B2 | 8/2013 | Narayan |
| 8,838,203 B2 | 9/2014 | Van Dam et al. |
| 8,849,389 B2 | 9/2014 | Anderson et al. |
| 9,014,795 B1 | 4/2015 | Yang |
| 9,129,053 B2 | 9/2015 | Mansi et al. |
| 9,277,970 B2 | 3/2016 | Mansi et al. |
| 9,320,126 B2 | 4/2016 | Valcore, Jr. |
| 9,706,935 B2 | 7/2017 | Spector |
| 9,842,725 B2 | 12/2017 | Valcore, Jr. |
| 9,948,642 B2 | 4/2018 | Wang |
| 10,039,454 B2 | 8/2018 | Sapp, Jr. et al. |
| 10,311,978 B2 | 6/2019 | Mansi et al. |
| 10,319,144 B2 | 6/2019 | Krummen et al. |
| 10,342,620 B2 | 7/2019 | Kiraly et al. |
| 10,363,100 B2 | 7/2019 | Trayanova et al. |
| 10,556,113 B2 | 2/2020 | Villongco |
| 10,617,314 B1 | 4/2020 | Villongco |
| 10,713,790 B2 | 7/2020 | Adler |
| 10,860,754 B2 | 12/2020 | Villongco |
| 10,861,246 B2 | 12/2020 | Voth |
| 10,912,476 B2 | 2/2021 | Spector |
| 10,952,794 B2 | 3/2021 | Villongco |
| 10,998,101 B1 | 5/2021 | Tran |
| 11,065,060 B2 | 7/2021 | Villongco |
| 11,259,871 B2 | 3/2022 | Villongco |
| 11,338,131 B1 | 5/2022 | Krummen |
| 2001/0049688 A1 | 12/2001 | Fratkina et al. |
| 2002/0010679 A1 | 1/2002 | Felsher |
| 2002/0154153 A1 | 10/2002 | Messinger |
| 2002/0188599 A1 | 12/2002 | McGreevy |
| 2003/0182124 A1 | 9/2003 | Khan |
| 2003/0195400 A1 | 10/2003 | Glukhovsky |
| 2004/0059237 A1 | 3/2004 | Narayan |
| 2004/0083092 A1 | 4/2004 | Valles |
| 2004/0153128 A1 | 8/2004 | Suresh et al. |
| 2004/0176697 A1 | 9/2004 | Kappenberger |
| 2007/0031019 A1 | 2/2007 | Lesage |
| 2007/0032733 A1 | 2/2007 | Burton |
| 2007/0060829 A1 | 3/2007 | Pappone |
| 2007/0219452 A1 | 9/2007 | Cohen et al. |
| 2008/0077032 A1 | 3/2008 | Holmes et al. |
| 2008/0140143 A1 | 6/2008 | Ettori |
| 2008/0177192 A1 | 7/2008 | Chen |
| 2008/0205722 A1 | 8/2008 | Schaefer |
| 2008/0234576 A1 | 9/2008 | Gavit-Houdant et al. |
| 2008/0288493 A1 | 11/2008 | Yang et al. |
| 2009/0088816 A1 | 4/2009 | Harel et al. |
| 2009/0099468 A1 | 4/2009 | Thiagalingam |
| 2009/0275850 A1 | 11/2009 | Mehendale |
| 2010/0016917 A1* | 1/2010 | Efimov ............... A61N 1/362 607/17 |
| 2010/0266170 A1 | 10/2010 | Khamene |
| 2011/0028848 A1 | 2/2011 | Shaquer |
| 2011/0118590 A1 | 5/2011 | Zhang |
| 2011/0251505 A1 | 10/2011 | Narayan |
| 2011/0307231 A1 | 12/2011 | Kirchner |
| 2012/0173576 A1 | 7/2012 | Gillam et al. |
| 2013/0006131 A1 | 1/2013 | Narayan |
| 2013/0035576 A1 | 2/2013 | O'Grady et al. |
| 2013/0096394 A1 | 4/2013 | Gupta |
| 2013/0131529 A1 | 5/2013 | Jia |
| 2013/0131629 A1 | 5/2013 | Jia |
| 2013/0150742 A1 | 6/2013 | Briggs |
| 2013/0197881 A1 | 8/2013 | Mansi et al. |
| 2013/0268284 A1 | 10/2013 | Heck |
| 2013/0304445 A1 | 11/2013 | Iwamura et al. |
| 2014/0005562 A1 | 1/2014 | Bunch |
| 2014/0088943 A1 | 3/2014 | Trayanova et al. |
| 2014/0107511 A1 | 4/2014 | Banet |
| 2014/0122048 A1 | 5/2014 | Vadakkumpadan et al. |
| 2014/0200575 A1 | 7/2014 | Spector |
| 2014/0276152 A1 | 9/2014 | Narayan |
| 2015/0005652 A1 | 1/2015 | Banet et al. |
| 2015/0057522 A1 | 2/2015 | Nguyen |
| 2015/0216432 A1 | 8/2015 | Yang |
| 2015/0216434 A1 | 8/2015 | Ghosh |
| 2015/0216438 A1 | 8/2015 | Bokan et al. |
| 2015/0294082 A1 | 10/2015 | Passerini et al. |
| 2016/0008635 A1 | 1/2016 | Burdette |
| 2016/0038743 A1 | 2/2016 | Foster et al. |
| 2016/0113725 A1 | 4/2016 | Trayanova et al. |
| 2016/0117816 A1 | 4/2016 | Taylor |
| 2016/0135702 A1 | 5/2016 | Perez |
| 2016/0135706 A1 | 5/2016 | Sullivan |
| 2016/0143553 A1 | 5/2016 | Chien |
| 2016/0192868 A1 | 7/2016 | Levant et al. |
| 2016/0331337 A1 | 11/2016 | Ben-Haim |
| 2017/0027649 A1 | 2/2017 | Kiraly |
| 2017/0061617 A1 | 3/2017 | Cochet |
| 2017/0065195 A1 | 3/2017 | Nguyen |
| 2017/0068796 A1 | 3/2017 | Passerini et al. |
| 2017/0079542 A1 | 3/2017 | Spector |
| 2017/0112401 A1 | 4/2017 | Rapin |
| 2017/0150928 A1 | 6/2017 | del Alamo de Pedro |
| 2017/0156612 A1 | 6/2017 | Relan |
| 2017/0161439 A1 | 6/2017 | Raduchel et al. |
| 2017/0161896 A1 | 6/2017 | Blake, III |
| 2017/0178403 A1 | 6/2017 | Krummen |
| 2017/0185740 A1* | 6/2017 | Seegerer ............... G09B 23/288 |
| 2017/0202421 A1 | 7/2017 | Hwang et al. |
| 2017/0202521 A1 | 7/2017 | Urman et al. |
| 2017/0209698 A1 | 7/2017 | Villongco |
| 2017/0231505 A1 | 8/2017 | Mahajan |
| 2017/0273588 A1 | 9/2017 | He |
| 2017/0027465 A1 | 11/2017 | Blauer |
| 2017/0319089 A1 | 11/2017 | Lou |
| 2017/0319278 A1 | 11/2017 | Trayanova |
| 2017/0330075 A1 | 11/2017 | Tuysuzoglu |
| 2017/0367603 A1 | 12/2017 | Spector |
| 2018/0012363 A1 | 1/2018 | Seiler |
| 2018/0020916 A1 | 1/2018 | Ruppersberg |
| 2018/0032689 A1 | 2/2018 | Kiranyaz |
| 2018/0260706 A1 | 9/2018 | Galloway et al. |
| 2018/0279896 A1 | 10/2018 | Ruppersberg |
| 2018/0317800 A1 | 11/2018 | Coleman et al. |
| 2018/0318606 A1 | 11/2018 | Robinson |
| 2018/0326203 A1 | 11/2018 | Hastings et al. |
| 2018/0333104 A1 | 11/2018 | Sitek |
| 2019/0038363 A1 | 2/2019 | Adler |
| 2019/0060006 A1 | 2/2019 | Van Dam |
| 2019/0069795 A1 | 3/2019 | Kiranya |
| 2019/0104951 A1 | 4/2019 | Valys |
| 2019/0104958 A1 | 4/2019 | Rappel |
| 2019/0125186 A1 | 5/2019 | Ruppersberg |
| 2019/0216350 A1 | 7/2019 | Sullivan et al. |
| 2019/0223946 A1 | 7/2019 | Coates |
| 2019/0304183 A1 | 10/2019 | Krummen |
| 2019/0328254 A1 | 10/2019 | Villongco |
| 2019/0328257 A1 | 10/2019 | Villongco |
| 2019/0328457 A1 | 10/2019 | Villongco et al. |

(56) References Cited

U.S. PATENT DOCUMENTS

| | | |
|---|---|---|
| 2019/0328458 A1 | 10/2019 | Shmayahu |
| 2019/0332729 A1 | 10/2019 | Villongco |
| 2019/0333639 A1 | 10/2019 | Villongco |
| 2019/0333641 A1 | 10/2019 | Villongco |
| 2019/0333643 A1 | 10/2019 | Villongco |
| 2020/0107781 A1 | 4/2020 | Navalgund et al. |
| 2020/0245935 A1 | 8/2020 | Krummen et al. |
| 2020/0324118 A1 | 10/2020 | Garner et al. |
| 2020/0405148 A1 | 12/2020 | Tran |
| 2021/0012868 A1 | 1/2021 | Wolf et al. |
| 2021/0015390 A1 | 1/2021 | Zhou et al. |
| 2021/0137384 A1 | 5/2021 | Robinson et al. |
| 2021/0205025 A1 | 7/2021 | Erkamp et al. |
| 2021/0219923 A1 | 7/2021 | Eun Young Yang |
| 2021/0251490 A1* | 8/2021 | Abdolmanafi ....... G06V 10/764 |
| 2021/0259560 A1 | 8/2021 | Venkatraman |
| 2022/0047237 A1 | 2/2022 | Liu |
| 2022/0370033 A1* | 11/2022 | Klingensmith ........ A61B 34/10 |

FOREIGN PATENT DOCUMENTS

| | | |
|---|---|---|
| CN | 107025618 A | 8/2017 |
| CN | 107951485 A | 4/2018 |
| CN | 113851225 A | 12/2021 |
| CN | 114206218 A | 3/2022 |
| JP | H4174643 A | 6/1992 |
| JP | H08289877 A | 11/1996 |
| JP | 2007517633 A | 7/2007 |
| JP | 2012508079 A | 4/2012 |
| JP | 2014530074 A | 11/2014 |
| JP | 2015163199 A | 9/2015 |
| JP | 2017-140381 A | 8/2017 |
| JP | 2018036996 A | 3/2018 |
| WO | 2006066324 A1 | 6/2006 |
| WO | 2015153832 A1 | 10/2015 |
| WO | 2015196140 A1 | 12/2015 |
| WO | 2016077154 A1 | 5/2016 |
| WO | 2018190715 A1 | 10/2018 |
| WO | 2019118640 A1 | 6/2019 |
| WO | 2020101864 | 5/2020 |
| WO | 2020142539 | 7/2020 |
| WO | 2022162329 A1 | 8/2022 |

OTHER PUBLICATIONS

Acharya et al., Deep convolutional neural network for the automated detection and diagnosis of seizure using EEG signals, Computers in Biology and Medicine (Sep. 1 2018, Epub Sep. 27 2017) 100:270-278.

Acharya UR, Fujita H, Lih OS, Hagiwara Y, Tan JH, Adam M. Automated detection of arrhythmias using different intervals of tachycardia ECG segments with convolutional neural network. Information sciences. Sep. 1, 2017 ;405:81-90.

Andreu et al., "Integration of 3D Electroanatomic Maps and Magnetic Resonance Scar Characterization Into the Navigation System to Guide Ventricular Tachycardia Ablation", Circ Arrhythm Electrophysiol, Oct. 2011, 4(5), pp. 674-683.

Bond et al., XML-BSPM: An XML Format for Storing Body Surface Potential Map Recordings, BMC Medical Informatics and Decision Making 2010, 10:28, http://www.biomedcentra.com/1472-6947/10/28, 27 pages.

Carrault, Guy, et al. "A model-based approach for learning to identify cardia arrhythias," Joint European Conference on Artificial Intellegence in Medicine and Medicine Decision Making. Springer, Berline Heidelberg, 1999.

Carrualt, Guy, et al. "Temporal abstraction and inductive logic programming for arrhythima recognition from electrocardiograms." Artificial intelligence in medicine 28.3 (2003): 231-263.

Cobb, Leonard A., et al. "Changing incidence of out-of-hospital ventricular fibrillation, 1980-2000." Jama 288.23 (2002): 3008-3013.

Cuculich, Phillip S. et al., "Noninvasive Cardiac Radiation for Ablation of Ventricular Tachycardia" New England Journal of Medicine, 377; 24, pp. 2325-2336, Dec. 14, 2017.

Dandu Ravi Varma, "Managing DICOM images: Tips and tricks for the radiologist", Indian J Radiol Imaging., Jan. 2012-Mar. 22(1), pp. 4-13.

Extended European Search Report issued in European Patent Application No. 19215701.4 and dated Apr. 17, 2020, 9 pages.

Extended European Search Report issued in European Patent Application No. 19792821.1 and dated Mar. 15, 2021. 10 pages.

Frank, Ernest, "An Accurate, Clinically Practical System for Spatial Vectorcardiography," American Heart Association, Inc., downloaded from http://circ.ahajournals.org/ at CONS California Dig Lib on Mar. 12, 2014.

Garg, et al., ECG Paper Records Digitization Through Image Processing Techniques, vol. 48, No. 13, Jun. 2012, 4 pages.

Goodfellow, Ian et al., Generative Adversarial Nets, Advances in Neural Information Processing Systems, pp. 2672-2680, 2014.

Gonzales, Matthew J., et al. "Structural contributions to fibrillatory rotors in a patient-derived computational model of the atria." EP Europace 16. suppl 4 (2014): iv3-iv10.

Graham, Adam J et al., "Evaluation of ECG Imaging to Map Haemodynamically Stable and Unstable Ventricular Arrhythmias" downloaded from http://ahajournals.org on Jan. 22, 2020.

Halevy, A., Norvig, P., & Pereira, F. (2009). The unreasonable effectiveness of data. IEEE intelligent systems, 24(2), 8-12.

He, Zhenliang et al., Facial Attribute Editing by Only Changing What You Want, IEEE Transactions on Image Processing, 2018.

Hershey S, Chaudhuri S, Ellis DP, Gemmeke JF, Jansen A, Moore RC, Plakal M, Platt D, Saurous RA, Seybold B, Slaney M. CNN architectures for large-scale audio classification. In2017 IEEE international conference on acoustics, speech and signal processing (icassp) Mar. 5, 2017 (pp. 131-135). IEEE.

Hren, Rok, et al. "Value of simulated body surface potential maps as templates in localizing sites of ectopic activation for radiofrequency ablation" Physiol. Meas. 18 (1997) 373-400. Mar. 7, 1997.

International Search Report and Written Opinion issued for PCT/US16/68449 dated Mar. 29, 2017.

International Search Report and Written Opinion issued for PCT/US2019/029181 dated Sep. 16, 2019.

International Search Report and Written Opinion issued for PCT/US2019/029184 dated Sep. 24, 2019.

International Search Report and Written Opinion issued for PCT/US2019/058217 dated Feb. 7, 2020, 9 pages.

International Search Report and Written Opinion issued for PCT/US2019/069136 dated May 11, 2020, 13 pages.

International Search Report and Written Opinion issued in PCT/US2020/036754 dated Oct. 15, 2020, 13 pages.

International Searching Authority, International Search Report and Written Opinion, PCT Patent Application PCT/US2021/057616, dated Jan. 28, 2022, 9 pages.

Jacquemet, V., "Lessons from Computer Simulation of Ablation of Atrial Fibrillation", J Physiol. 594(9): 2417-2430, May 1, 2016.

JPO, Notice of Reasons for Refusal for Japanese Patent Application No. 2018-527085, dated Dec. 23, 2020. 14 pages with English translation.

Kiranyaz et al., Real-time patient-specific EDG classification by 1-D convolutional neural networks, IEEE Transactions on Biomedical Engineering (Mar. 2016) 63:664-675.

Kiranyaz S, Ince T, Hamila R, Gabbouj M. Convolutional neural networks for patient-specific ECG classification. In2015 37th Annual International Conference of the IEEE Engineering in Medicine and Biology Society (EMBC) Aug. 25, 2015 (pp. 2608-2611). IEEE.

Kors, J.A., et al., "Recontruction of the Frank vectorcardiogram from standard electrocardiogramads: diagnostic comparison of different methods," European Heart Journal, vol. 11, Issue 12, Dec. 1, 1990, pp. 1083-1092.

Krishnamurthy, Adarsh, et al. "CRT Response is Greater in Patients With Larger Fraction of the Myocardium Performing Negative Regional Work." Circulation 128.Suppl 22 (2013): A11135-A11135, Abstract only.

Krishnamurthy, Adarsh, et al. "Patient-specific models of cardiac biomechanics." Journal of computational physics 244 (2013): 4-21.

(56) References Cited

OTHER PUBLICATIONS

Krummen, David E., et al. "Rotor stability separates sustained ventricular fibrillation from selfterminating episodes in humans." Journal of the American College of Cardiology 63.24 (2014): 2712-2721.
Lee H, Kwon H. Going deeper with contextual CNN for hyperspectral image classification. IEEE Transactions on Image Processing, Jul. 11, 2017;26(10): 4843-55.
Li D, Zhang J, Zhang Q, Wei X. Classification of ECG signals based on 1 D convolution neural network. In2017 IEEE 19th International Conference on e-Health Networking, Applications and Services (Healthcom) Oct. 12, 2017 (pp. 1-6). IEEE.
Light, D., E., et al. "Two Dimensional Arrays for Real Time Volumetric and Intracardiac Imaging with Simultaneous Electrocardiagram", 1196-2000 IEEE Ultrasonics Symposium, retrieved on Sep. 24, 2021.
Lyon, et al. J.R. Soc Interface vol. 15:1-18. (2017).
Nash, Martyn P., et al. "Evidence for multiple mechanisms in human ventricular fibrillation." Circulation 114.6 (2006): 536-542.
Office Action dated Mar. 18, 2021, Canada App. 3080944.
Office Action Response filed Mar. 23, 21, U.S. Appl. No. 17/082,892.
Pan, J., S., et al., "A Survey on Transfer Learning," IEEE Transactions on Knowledge and Data Engineering, vol. 22, No. 10, Oct. 2010, 15 pages.
Potse, Mark et al., "Continuos Localization of Cardian Activation Sites Using a Database of Multichannel ECG Recordings" IEEE Transactions of Biomedical Engineering, vol. 47, No. 5, May 2000, pp. 682-689.
Rahhal et al., Convolutional neural networks for electrocardiogram classification, Journal of Medical and Biological Engineering (Mar. 30, 2018) 38: 1014-1025.
Ravichandran et al., Novel Tool for Complete Digitization of Paper Electrocardiogra Data, vol. 1, 2013, 7 pages.
Sapp et al., "Real-Time Localization of Ventricular Tachycardia Origin From the 12-Lead Electrocardiogram", JACC Clinical Electrophysiology, vol. 3, No. 7, Jul. 2017.
Sapp, John L. et al., "Real-Time Localization of Ventricular Tachycardia Origin From the 12-Lead Electrocardiogram" JACC: Clinical Electrophysiology by the Amercian College of Cardiology Foundation, vol. 3, 2017, pp. 687-699.
Sharma, et al., Digitalization of ECG Records, International Journal of Engineering Research and Applications, www.ijera.com, ISSN: 2248-9622, vol. 10, Issue 6, (Series-VIII) Jun. 2020, pp. 01-05.
Shin HC, Roth HR, Gao M, Lu L, Xu Z, Nogues I, Yao J, Mollura D, Summers RM. Deep convolutional neural networks for computer-aided detection: CNN architectures, dataset characteristics and transfer learning. IEEE transactions on medical imaging. Feb. 11, 2016;35(5): 1285-98.
Si, Hang, "TetGen, a Delaunay-Based Quality Tetrahedral Mesh Generator," ACM Transactions on Mathematical Software, vol. 41, No. 2, Article 11, Jan. 2015, 36 pages.
Siregar, P. "An Interactive Qualitative Model in Cardiology" Computers and Biomedical Research 28, pp. 443-478, May 16, 1994.
Taggart, Peter, et al. "Developing a novel comprehensive framework for the investigation of cellular and whole heart electrophysiology in the in situ human heart: Historical perspectives, current progress and future prospects." Progress in biophysics and molecular biology 115.2-3 (2014): 252-260.
Tajbakhsh, Nima et al., "Convolutional Neural Networks for Medical Image Analysis: Full Training or Fine Tuning?" IEEE Transactions on Medical Imaging (2016) vol. 35, e-pp. 1-17).
Ten Tusscher et al. "A model for human ventricular tissue." Amerian Journal of PhysioloQy—Heart and Circulatory PhysioloQy 286.4 (2004): H1573-H1589.
Thakor and Tong (Annual Reviews in Biomedicine and Engineering (2004) vol. 6, 453-495).
Therrien R, Doyle S. Role of training data variability on classifier performance and generalizability. In Medical Imaging 2018: Digital Pathology Mar. 6, 2018 (vol. 10581, p. 1058109). International Society for Optics and Photonics.
Tobon, Catalina, et al. "Dominant frequency and organization index maps in a realistic three-dimensional computational model of atrial fibrillation." Europace; 14, suppl_5 (2012): v25-v32.
Tomašić, Ivan et al., "Electrocardiogramatems With Reduced Nos. of Leads—Synthesis of the 12-Lead ECG," IEEE Reviews in Biomedical Engineering, vol. 7, 2014, pp. 126-142.
USPTO, Final Office Action received for U.S. Appl. No. 16/444,340, dated Dec. 23, 2020. 9 pages.
USPTO, Non-Final Office Action received for U.S. Appl. No. 16/295,934, dated Dec. 23, 2020. 12 pages.
USPTO, Restriction Requirement received for U.S. Appl. No. 17/082,892, dated Feb. 2, 2021. 8 pages.
USPTO, Non-Final Office Action received for U.S. Appl. No. 17/082,892, dated Mar. 1, 2021. 33 pages.
USPTO, Non-Final Office Action received for U.S. Appl. No. 17/082,835, dated Jan. 29, 2021. 22 pages.
USPTO, Office Action dated Apr. 5, 2021, U.S. Appl. No. 17/082,835.
USPTO, Office Action dated Apr. 12, 2021, U.S. Appl. No. 17/082,892.
USPTO, Office Action dated Apr. 15, 2021, U.S. Appl. No. 16/043,054.
USPTO, Office Action dated Jul. 14, 2021, U.S. Appl. No. 16/247,463.
Vadakkumpadan, Fijoy, et al. "Image-based estimation of ventricular fiber orientations for personalized modeling of cardiac electrophysiology." IEEE-TMI 31.5 (2012): 1051-1060.
Villongco, Christopher T., et al. "Patient-specific modeling of ventricular activation pattern using surface ECG-derived vectorcardiogram in bundle branch block." Progress in biophysics and molecular biology 115.2 (2014): 305-313.
Vozda, M. et al., "Methods for derivation of orthogonal leads from 12-lead electrocardiogram: A review," Elsevier, Biomedical Signal Processing and Control 19 (2015), 23-34.
Xiong et al. Computing and Cardiology vol. 44: pp. 1-4. (2017).
Zentara, et al., ECG Signal Coding Methods in Digital Systems, Communication Papers of the Federated Conference on Computer Science and Information Systems,DOI: 10.15439/2018F108, ISSN 2300-5963 ACSIS, vol. 17, pp. 95-102.
Zhang, C., et al. "Patient-Specific ECG Classification Based on Recurrent Neural Networks and Clustering Technique," Proceedings of the IASTED International Conference in Biomedical Engineering (Bio Med 2017); Feb. 20-21, 2017, in Innsbruck, Austria, 5 pages.
Zhou, Shijie et al. "Localization of ventricular activation origin using patient-specific geometry: Preliminary results" J. Carciovasc Electrophysiol, 2018; 29: pp. 979-986.
Zhou, Shijie et al. "Rapid 12-lead automoated localization method: Comparison to electrocardiogramaging (ECGI) in patient-specific geometry", Journal of Electrocardiology, vol. 51, 2018, pp. S92-S97.
Zhu X, Vondrick C, Fowlkes CC, Ramanan D. Do we need more training data?. International Journal of Computer Vision.Aug. 2016;119(1):76-92.
Zubair M, Kim J, Yoon C. An automated ECG beat classification system using convolutional neural networks. In2016 6th international conference on IT convergence and security (ICITCS) Sep. 26, 2016 (pp. 1-5). IEEE.
Hill et al., Investigating a Novel Activation-Repolarisation Time Metric to Predict Localised Vulnerability to Reentry Using Computational Modelling. Journal: PLoS ONE. Mar. 2, 2016. [Retrieved]: Nov. 30, 2022. Retrieved from <https://www.semanticscholar.org/paper/Investigating-a-Novel-Activation-Repolarisation-to-Hill-Child/1689ac6a060dd0dbde1c01db41074dd35a81308e>entire document.

\* cited by examiner

MACHINE LEARNING FOR IDENTIFYING CHARACTERISTICS OF A REENTRANT CIRCUIT

CROSS-REFERENCE TO RELATED APPLICATION(S)

This application is a continuation of International Application PCT/US22/39627, filed Aug. 5, 2022, entitled "TISSUE STATE GRAPHIC DISPLAY SYSTEM" which claims the benefit of priority to U.S. application Ser. No. 63/231,022 filed on Aug. 9, 2021, and this application is a continuation of U.S. application Ser. No. 17/882,426, filed Aug. 5, 2022, entitled "TISSUE STATE GRAPHIC DISPLAY SYSTEM," which claims the benefit of priority to U.S. application Ser. No. 63/231,022 filed on Aug. 9, 2021, which are hereby incorporated by reference in its entirety.

BACKGROUND

Many heart disorders can cause symptoms, morbidity (e.g., syncope or stroke), and mortality. Common heart disorders caused by arrhythmias include inappropriate sinus tachycardia (IST), ectopic atrial rhythm, junctional rhythm, ventricular escape rhythm, atrial fibrillation (AF), ventricular fibrillation (VF), focal atrial tachycardia (focal AT), atrial micro reentry, ventricular tachycardia (VT), atrial flutter (AFL), premature ventricular complexes (PVCs), premature atrial complexes (PACs), atrioventricular nodal reentrant tachycardia (AVNRT), atrioventricular reentrant tachycardia (AVRT), permanent junctional reciprocating tachycardia (PJRT), and junctional tachycardia (JT). The sources of arrhythmias may include electrical rotors (e.g., VF), recurring electrical focal sources (e.g., AT), anatomically based reentry (e.g., VT), and so on. These sources are important drivers of sustained or clinically significant episodes. Arrhythmias can be treated with ablation using different technologies—including radiofrequency energy ablation, cryoablation, ultrasound ablation, laser ablation, external radiation sources, directed gene therapy, and so on—by targeting the source of the heart disorder. Since the sources of heart disorders and the locations of the source vary from patient to patient, even for common heart disorders, targeted therapies require the source of the arrhythmia to be identified.

Unfortunately, traditional methods for reliably identifying the sources and the source locations of a heart disorder can be complex, cumbersome, and expensive. For example, one method uses an electrophysiology catheter having a multi-electrode basket catheter that is inserted into the heart (e.g., left ventricle) intravascularly to collect measurements of the electrical activity of the heart, such as during an induced episode of VF. The measurements can then be analyzed to help identify a source location. Presently, electrophysiology catheters are expensive (and generally limited to a single use) and may lead to serious complications, including cardiac perforation and tamponade. Another method uses an exterior body surface vest with electrodes to collect measurements from the patient's body surface, which can be analyzed to help identify an arrhythmia source location. Such body surface vests are expensive, are complex and difficult to manufacture, and may interfere with the placement of defibrillator pads needed after inducing VF to collect measurements during the arrhythmia. In addition, the vest analysis requires a computed tomography (CT) scan, and a body surface vest is unable to sense the interventricular and interatrial septa where approximately 20% of arrhythmia sources may occur.

Knowledge of the cardiac tissue state collected from a patient can be helpful in evaluating the patient's cardiac function. Various techniques have been used to categorize cardiac tissue state as normal or abnormal. Abnormal cardiac tissue may indicate border zone tissue or scar tissue. Some techniques support determining cardiac tissue state based on perfusion through the cardiac tissue, based on motion of the heart wall, based on electrical activity, and so on. Although cardiac tissue state can be used to identify areas of the heart whose function is normal or abnormal, the cardiac tissue state by itself cannot typically be used to determine the precise source location of an arrhythmia.

DETAILED DESCRIPTION

Figure 1:
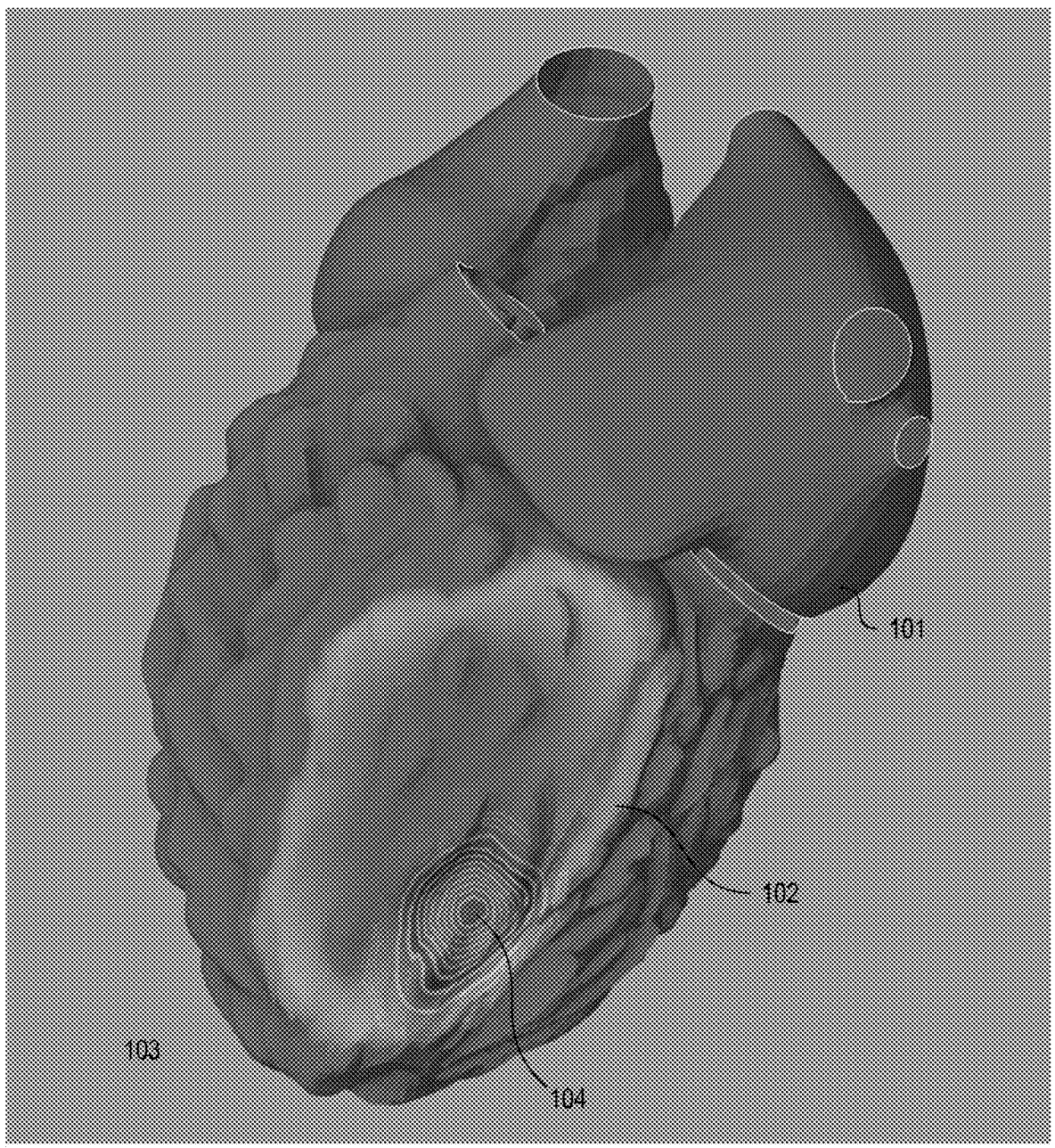
FIG. 1 illustrates a 3D graphic of a heart indicating tissue state.

Methods and systems are provided for displaying a graphic indicating areas of tissue state (normal or abnormal) of the tissue of an organ within a subject and indicating a source location of a source of abnormal electrical activity of the organ. The subject may be a human or an animal, and the organ may be, for example, a heart, a brain, a digestive organ, a lung, a liver, a kidney, a stomach, or a skeletal muscle whose activity can be measured, preferably, noninvasively (e.g., from outside the body of the subject) or minimally invasively. The tissue state may represent activity of the organ, such as electrical, metabolic, motion, or perfusion, that ranges from normal to abnormal. The tissue state may also be represented by other characteristics such as organ wall thickness. The tissue state may be categorized, for example, as normal tissue, border zone tissue, and scar tissue that ranges from normal to no electrical activity, normal to no metabolic activity, normal to no perfusion, normal to limited motion, and normal to minimal wall thickness. The tissue state may be derived from scans or other measurements of the organ of the subject (subject organ). The scans may include, for example, one or more of sestamibi, positron emission tomography (PET), echography, computed tomography, voltage mapping, and magnetic resonance imaging (MRI) scans. In the following, a Tissue State Graphic Display (TSGD) system is described primarily in the context of an organ that is a heart. The methods and systems of the TSGD system that are described below for the heart can be employed to provide graphics for other organs. A graphic provides a multidimensional representation of a heart, such as a two-dimensional (2D), three-dimensional (3D), or four-dimensional (4D) representation, which provides visual indications of tissue state and the source location of abnormal electrical activity (e.g., an arrhythmia). The term "patient heart" is used to refer to the entire patient heart or a portion of the patient heart, such as the left atrium or right ventricle.

As described above, the electrical tissue state may be categorized as normal, border zone, or scar tissue, with the latter two being abnormal tissue states. Border zone tissue is tissue between normal tissue and scar tissue and exhibits activity that is between that of normal tissue and scar tissue. Abnormal tissue often includes a source of abnormal electrical activity that is initiated by cells at a source location. The electrical activity may initiate at a source location within border zone tissue (or within an area of scar tissue) and propagate through the border zone tissue to the normal tissue. The location at which the electrical activity exits the border zone tissue is referred to as an "exit site." The electrical activity may represent various types of arrhythmias, such as an AF or VF. To prevent such abnormal electrical activity, an electrophysiologist (EP) may perform an ablation procedure targeting the cells near the source location and possibly targeting the cells of all the border zone and scar tissue. One noninvasive technique for identifying a source location (or a source area) is described in U.S. Pat. No. 10,860,754 entitled "Calibration of Simulated Cardiograms" and issued on Dec. 18, 2020, which is hereby incorporated by reference.

In some embodiments, the TSGD system displays a graphic to provide information on areas of tissue state that range from normal to abnormal and the source location of an arrhythmia of a patient (a subject). An EP may use the information to assist in developing a course of treatment for the patient, such as deciding where to initially position a catheter to start pacing to determine the target of the ablation. A graphic may have a geometry that is based on a generic geometry or a patient-specific geometry. The geometry of the patient heart may be determined based on measurements collected from the patient (e.g., via echocardiography, CT, and anatomical mapping), that is identified based on simulations using different heart geometries (e.g., as described in U.S. Pat. No. 10,952,794 entitled "Augmentation of Images with Source Location" issued on Mar. 23, 2021, which is hereby incorporated by reference). The different tissue states may be represented by different colors, such as a range of colors from blue for normal perfusion to red for no perfusion. The TSGD system also adds to the graphic an indication of the source location, which may be illustrated as contours representing the probability of the source location being within each contour, with the center contour representing the highest likelihood. The probabilities may also be represented by colors that are different from the colors used for the tissue state. FIG. 1 illustrates a 3D graphic with normal tissue 101, border zone tissue 102, and scar tissue 103 illustrated in black, gray, and red, respectively. The source location 104 is illustrated with contours. (Note: If the drawings are not available in color, the colors are represented by various intensities of a grayscale.)

The TSGD system identifies the tissue state (e.g., level of perfusion) from scans of the patient heart. A scan typically generates 2D images representing slices of a heart. Each 2D image may include colors to indicate the tissue state in the portion of the patient heart represented by the 2D image. The tissue state may alternatively be identified in metadata associated with the 2D images, such as metadata that includes a color or other identifier of the tissue state for each pixel of the image. The metadata may also indicate the portion of the patient heart that the slice represents, such as an orientation and a location on the heart wall. For each 2D image, the TSGD system maps that 2D image to a corresponding 3D model slice of a 3D model of a heart representing a heart geometry and including an indication of a source location. The TSGD system then adds to that 3D model slice (directly or via metadata) a specification of the tissue state represented by the 2D image. The 3D model may also represent different sublayers of layers of the heart wall. The layers of a heart include the endocardium, myocardium, and epicardium. The myocardium may have, for example, 16 sublayers spanning the thickness of the myocardium. When a 3D graphic is generated based on the 3D model, the tissue state for a selected sublayer may be displayed. When different sublayers are selected for display (e.g., by a user), an EP may analyze the sublayers to assess the full extent (volume) of the tissue state and source location. In addition, the TSGD system may also display a 2D graphic representing a 3D model slice of the 3D model. Such a 2D graphic represents the tissue state and source location across all the sublayers of the heart wall. The TSGD system may also adjust the 3D model based on the geometry of the patient heart represented by the 2D images.

The TSGD system may represent the 3D model (e.g., of FIG. 1) in a Digital Imaging and Communications in Medicine (DICOM) formatted file (possibly as metadata) and provide the DICOM file to an external system that identifies areas of normal, border zone, and scar tissue that may be different from those of the 3D model. The external system may superimpose the identified areas onto the 3D model represented by the DICOM file. Other file formats may be used, such as a stereolithography (STL) format or an OBJ file format. The overlapping and nonoverlapping areas of the 3D model and those identified by the external system may be illustrated using different colors, cross-hatching, shading, and so on. For example, the areas of scar tissue that overlap may be illustrated in dark red, and the areas that do not overlap may be illustrated in different shades of red to differentiate the nonoverlapping areas of the scar tissue of the exported 3D model and the scar tissue identified by the external system. The external system may also adjust the heart geometry of the 3D graphic and areas of different tissue states and the source location based on heart geometry identified by the external system.

In the following, the TSGD system is described as applied to various modalities for tissue state identification.

Sestamibi

Figure 2:
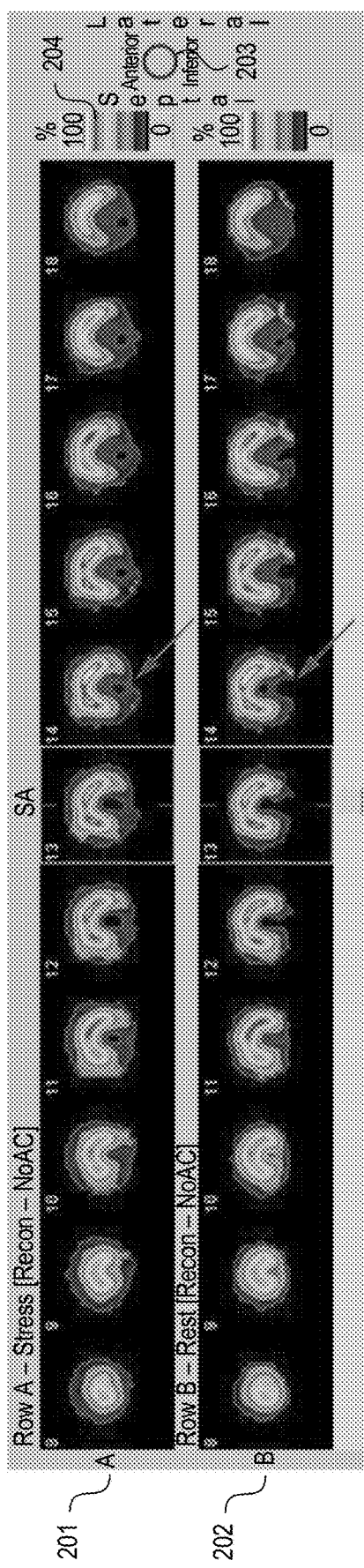
FIG. 2 illustrates a sestamibi image that indicates the amount of perfusion within regions of a left ventricle.

With sestamibi, images are collected from a patient with a radioactive dye that releases gamma rays injected into the blood stream. By measuring the gamma ray emissions, perfusion through the tissue can be quantified to differentiate normal, border zone, and scar tissue. FIG. 2 illustrates a sestamibi image that indicates the amount of perfusion within regions of a left ventricle. The legend 203 indicates the orientation of the left ventricle with anterior at the top and septal to the left. The top row 201 illustrates perfusion during stress (e.g., during a treadmill test), and the bottom row 202 illustrates perfusion at rest. The legend 204 represents a color scale of the amount of perfusion, ranging from 100% full perfusion (normal tissue) in red to 0% perfusion (scar tissue) in purple. The range corresponding to border zone tissue may be set to be in a range, for example, between 25% and 75%. Each image in a row represents different slices of the left ventricle. The TSGD system maps the slices to the myocardium of the 3D model and superimposes a source location as illustrated in FIG. 1.

PET

Figure 3:
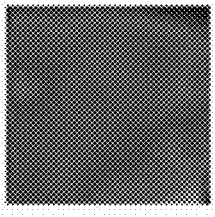
FIG. 3 illustrates images representing different tissue states.

With PET, images are collected from a patient with a radioactive dye that releases positrons injected into the bloodstream. By measuring the positron emissions, perfusion through the tissue and metabolism of the tissue can be quantified to indicate normal, border zone, and scar tissue. FIG. 3 illustrates images representing different tissue states. The images 301 represent perfusion ranging from normal (top) to no or minimal perfusion (bottom). The images 302 represent metabolism as measured by fluorodeoxyglucose (FDG) uptake by the cells. The top and bottom images represent no (or minimal) FDG update, and the images in between represent FDG uptake. The disease state (e.g., scar tissue) is indicated based on a combination of perfusion and FDG uptake. For example, as illustrated by the second images from the top, a minimally reduced perfusion (indicated in yellow) combined with FDG uptake (indicated in yellow) represent a mild disease state or border zone tissue. The TSGD system maps the images to 3D model slices of the 3D model and superimposes a source location as illustrated in FIG. 1.

Echocardiogram

Figure 4:
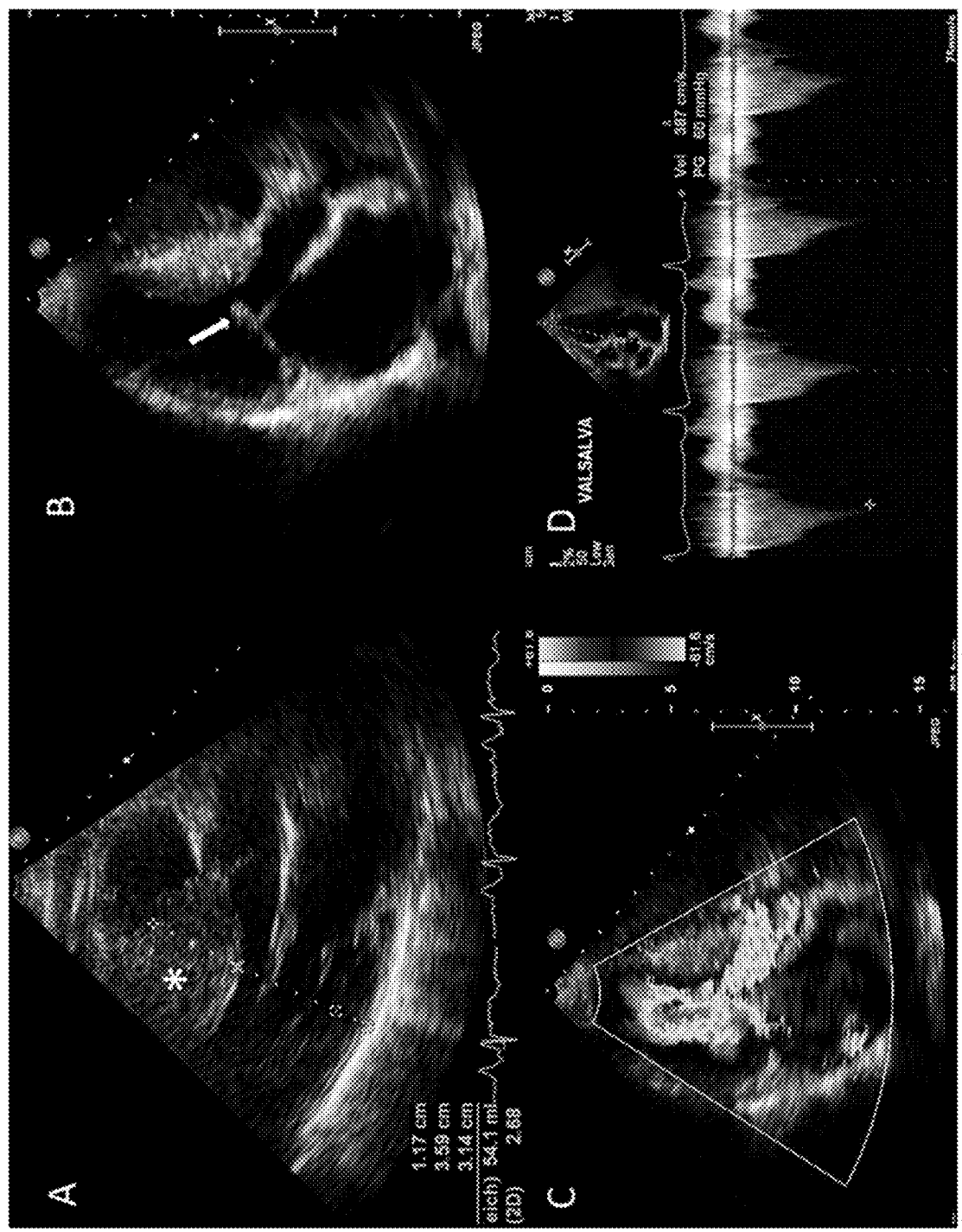
FIG. 4 illustrates echocardiogram images.

With an echocardiogram, images are collected using transthoracic, esophageal, or intracardiac imaging. The images can be analyzed to identify normal motion, reduced motion, and significantly reduced motion, which correspond to normal tissue, border zone tissue, and scar tissue, respectively. The images can also be analyzed to determine cardiac wall thickness to identify normal thickness, reduced thickness, and significantly reduced thickness, corresponding to normal tissue, border zone tissue, and scar tissue. FIG. 4 illustrates echocardiogram images. The motion refers to movement of the myocardium as the heart contracts and expands. Given a sequence of images, the pixels corresponding to a point on the myocardium during contraction and expansion can be analyzed to determine the distance the point moves as an assessment of motion. Significant, moderate, and minimal movement indicate normal, border zone, and scar tissue, respectively. The thickness refers to the thickness of myocardium resulting from strain during contraction and expansion. The thickness of normal tissue increases and decreases during contraction and expansion. In contrast, the thickness of scar tissue tends not to change (at least not much) during contraction and expansion. Given a sequence of images, pixels corresponding to points on the endocardium and the epicardium can be analyzed from one image to the next to determine the thickness. The thickness may be assessed based on a point on the endocardium and the closest point of the epicardium. The TSGD system maps the assessment of normal, border zone, and scar tissue determined based on the motion and thickness of the myocardium of 3D model and superimposes a source location as illustrated in FIG. 1. A transesophageal echocardiogram may also be used to collect intracardiac images as a sequence of 3D images, referred to as a 4D image, which is analyzed to determine motion and wall thickness.

CT Imaging

With CT images, images are collected with contrast material that may be injected into the bloodstream. Normally, the amount of contrast dye used is the minimal amount needed to determine blood flow through blood vessels. However, if the amount of contrast dye is increased, perfusion within the cardiac tissue can be quantified. Given the quantification of the perfusion, techniques similar to those described above (e.g., sestamibi imaging) can be used to identify and map normal, border zone, and scar tissue to a 3D model with the source location superimposed.

Figure 5:
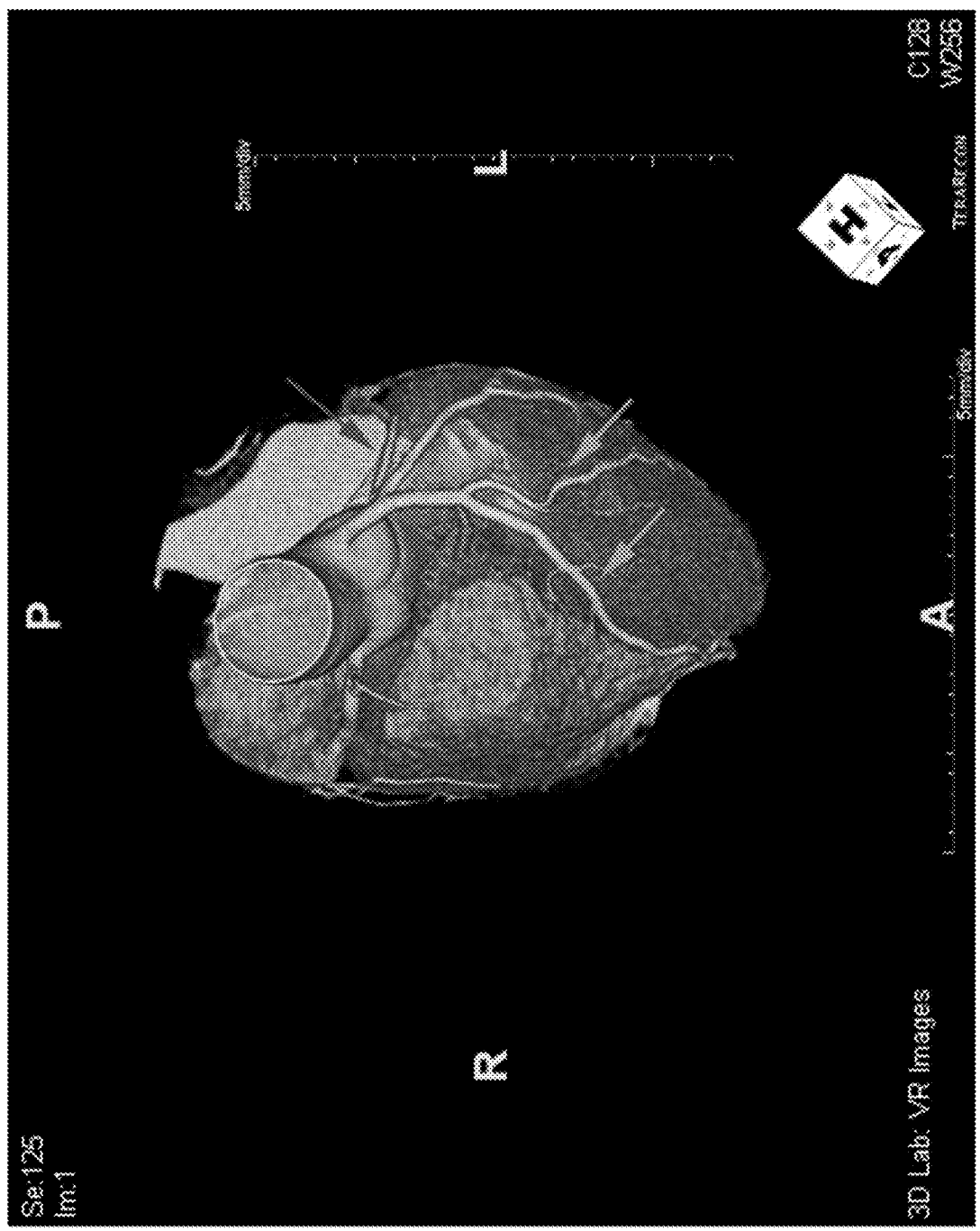
FIG. 5 illustrates cardiac arteries with normal and severely restricted blood flow.

CT images collected with even a normal amount of contrast material can be used to assess blood flow in the cardiac arteries. A portion of a cardiac artery with little or no blood flow (e.g., significant calcium deposits) may indicate that scar tissue has formed nearby. The TSGD system generates a 3D model that indicates the amount of blood flow through portions of the cardiac arteries. FIG. 5 illustrates cardiac arteries with normal and severely restricted blood flow. The green arrows and red arrows point to portions of normal blood flow and severely restricted blood flow, respectively. The amount of blood flow may also be illustrated by overlaying the cardiac arteries, for example, with red to indicate normal blood flow, transitioning to gray to indicate restricted blood flow, and transitioning to black to indicate severely restricted or no blood flow. With the source location superimposed on a 3D graphic, a cardiologist would be able to assess more effectively, for example, an ablation target.

Voltage Map

Figure 6:
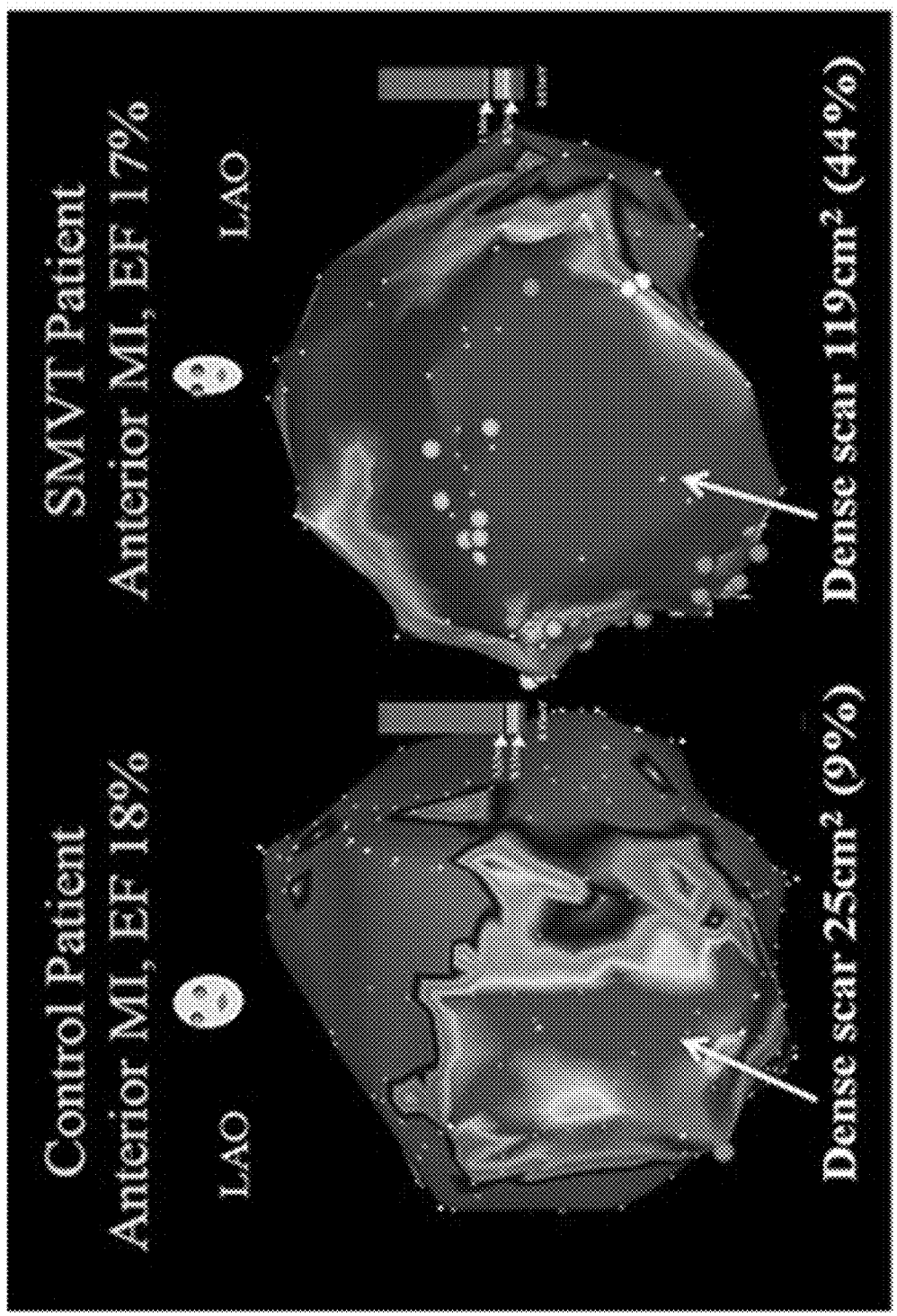
FIG. 6 illustrates a voltage map.

A cardiac voltage map may be collected, for example, with a basket catheter. FIG. 6 illustrates a voltage map. The red areas represent scar tissue, and the yellow and blue areas represent border zone tissue. The TSGD system may superimpose the source location on a 2D voltage map. The TSGD system may also map the voltage map to a 3D graphic with the source location superimposed as illustrated in FIG. 1.

MRI

Figure 7:
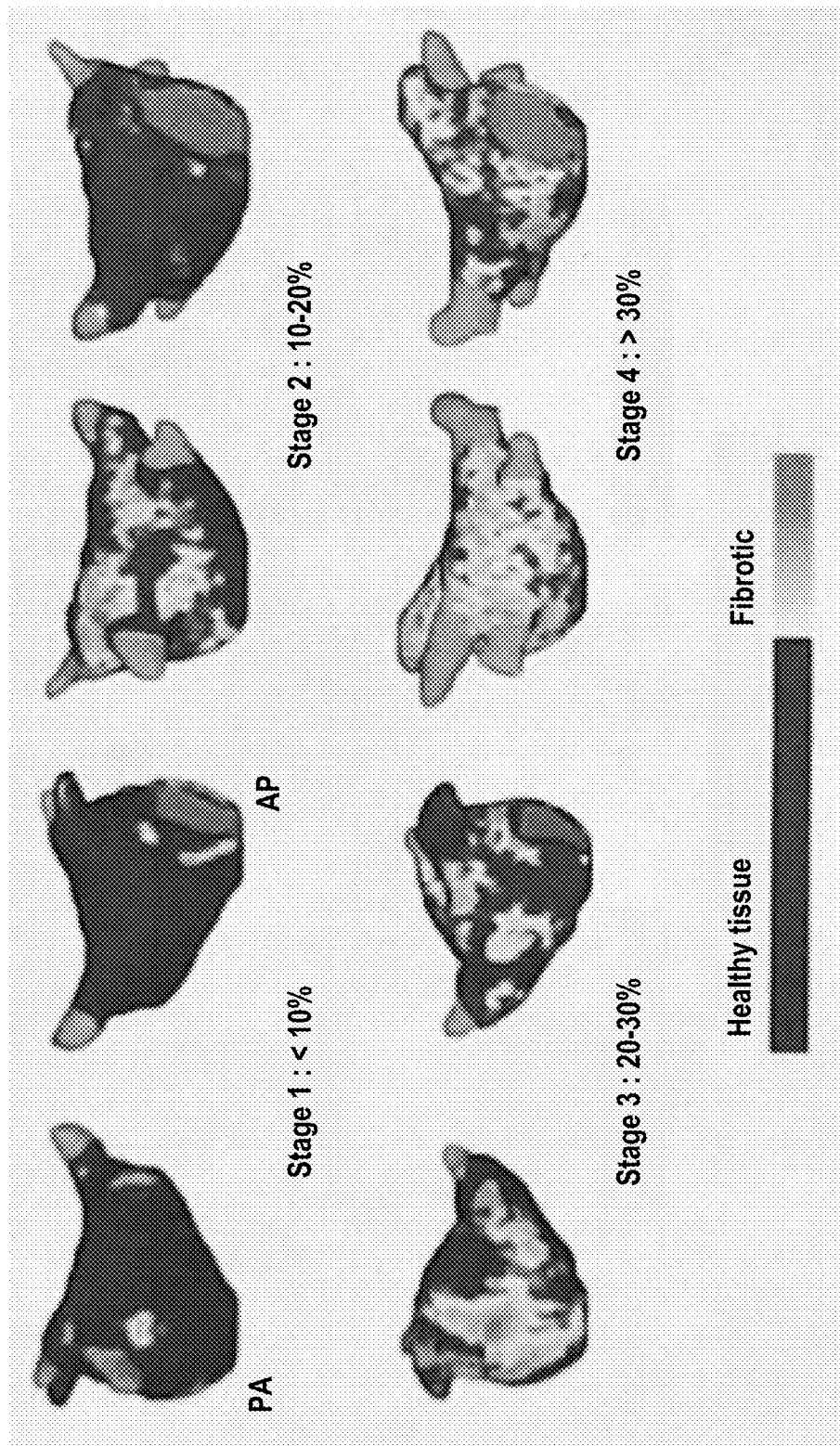
FIG. 7 illustrates MRI images of an atrium.
Figure 8:
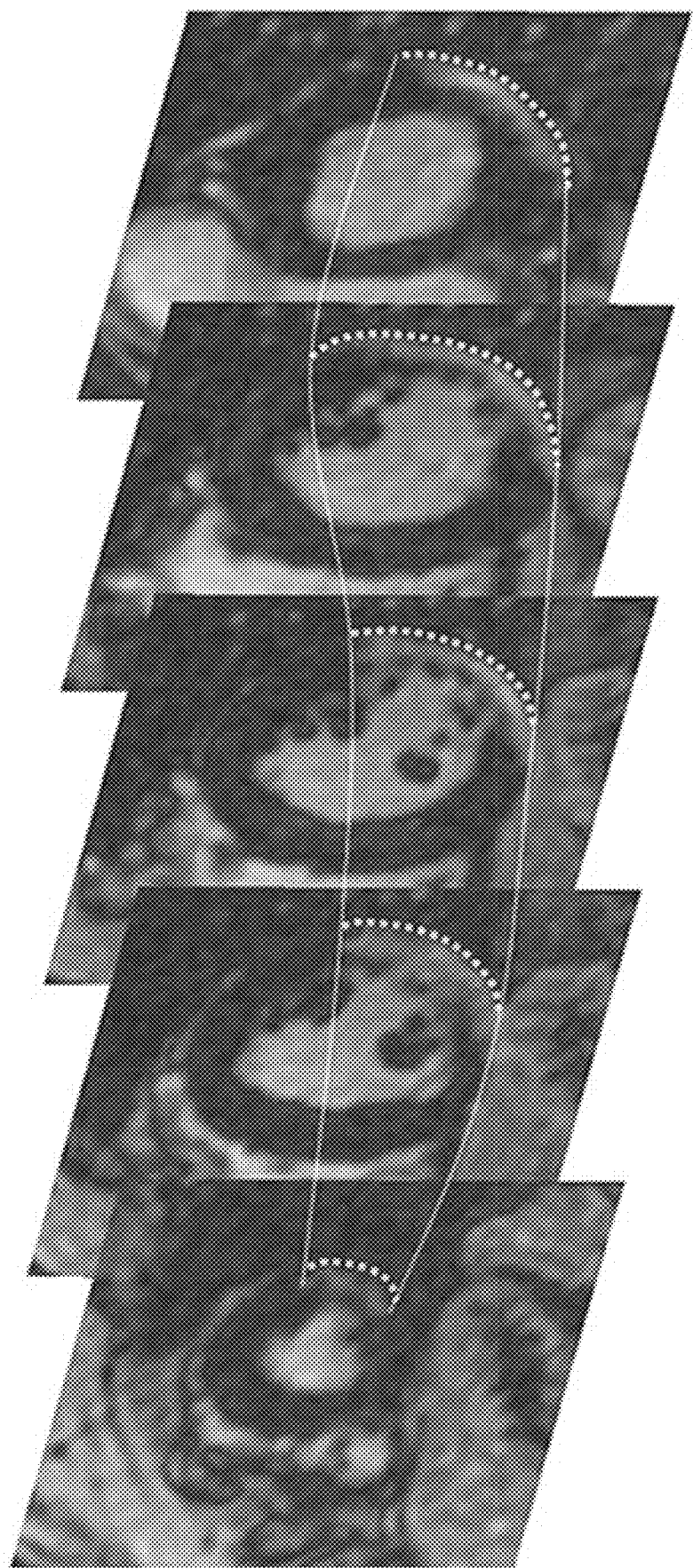
FIG. 8 illustrates MRI images representing slices of a left ventricle.

With MRI imaging, images may be collected from a patient with contrast dye injected in the patient's blood to quantify the amount of perfusion in the cardiac tissue. FIG. 7 illustrates MRI images of an atrium. The blue indicates normal tissue, and the green indicates scar tissue (e.g., fibrotic). FIG. 8 illustrates MRI images representing slices of a left ventricle. The yellow dotted lines represent the location of reduced perfusion, indicating scar tissue. The TSGD system may generate a 3D model in a manner similar to that described above for sestamibi imaging.

Reentry Machine Learning System

Figure 9:
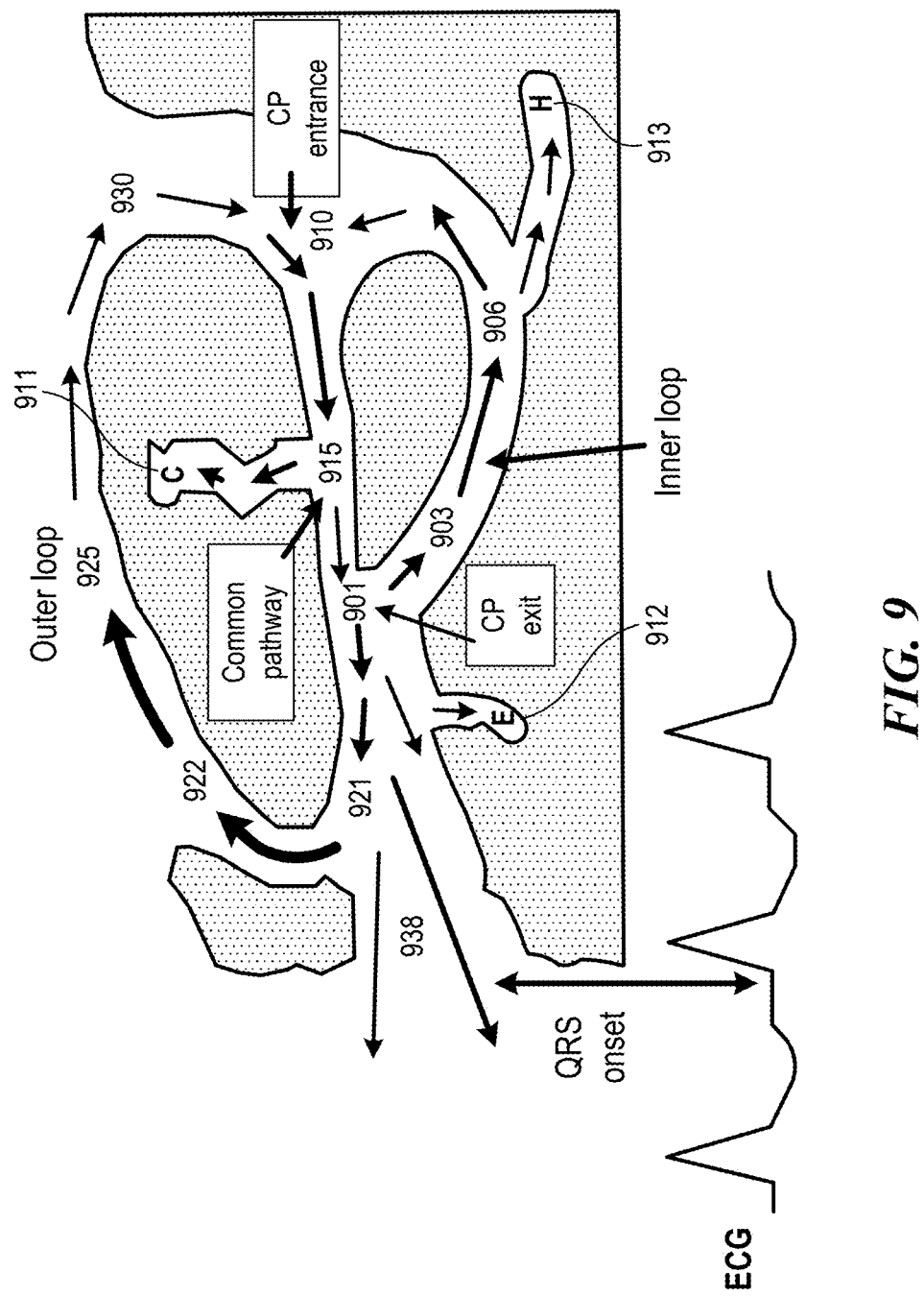
FIG. 9 is a diagram that provides a 2D illustration of an example reentrant circuit.

A reentry machine learning (RML) system is provided to identify an entrance site, an isthmus, and/or an exit site of a reentrant circuit of a reentrant arrhythmia based at least on the tissue state of the reentrant circuit. The exit site may be a target for an ablation to terminate the functioning of the reentrant circuit. The source location of electrical activity that results in the activation of the reentrant circuit may be within or outside of the reentrant circuit. FIG. 9 is a diagram that provides a 2D illustration of an example reentrant circuit. A common pathway (CP) 915 (e.g., isthmus) between scar tissue is the path leading from CP entrance site 910 to CP exit site 901. An inner loop 901, 903, 906, and 910 leads from the CP exit site to the CP entrance site. An outer loop 901, 921, 922, 925, 930, and 910 leads from the CP exit site to the CP entrance site. Channels C 911, E 912, and H 913 are dead-end channels in which action potential enters the dead-end channel and terminates within the dead-end channel. The RML system may generate a 3D reentrant model of a reentrant circuit that is derived from a 3D model of a heart that includes a specification of the tissue state that is generated by the TSGD system or derived from some other system.

In some embodiments, the RML system trains an RML model using training data that specifies characteristics of reentrant circuits that may include an entrance site, an exit site, isthmus characteristics (e.g., path), and tissue characteristics that may include shape (e.g., 3D), location, and properties (e.g., perfusion, electrical, motion, etc.). The training data may be based on clinical data collected from subjects and/or simulated data. The clinical data may be collected by analyzing tissue state characteristics (e.g., perfusion or electrical activity) of reentrant circuits of subjects. The simulated data may be generated by simulating electrical activity of a heart assuming certain tissue characteristics.

The simulating of the electrical activity of a heart is described in U.S. Pat. No. 11,259,871 entitled "Identify Ablation Pattern for Use in an Ablation" and issued on Mar. 1, 2022, which is hereby incorporated by reference. The simulation employs a 3D mesh with vertices representing locations within the heart and having electrical characteristics such as conduction velocity and action potential. Scar tissue may be represented as vertices with characteristics that have no electrical activity, and border zone tissue may be represented as vertices with characteristics that have limited electrical activity. Each simulation may have parameters that specify one or more areas of tissue (e.g., scar tissue and border zone tissue) which may emerge as functioning as a reentrant circuit during the simulation. The areas used in the simulations may be derived from a library of 2D images indicating tissue state (e.g., of reentrant circuits) that are collected from patients. The areas may be augmented with additional areas that are a modification of the areas derived from the 2D images. Alternatively, or in addition, the RML system may generate the areas using an algorithm based on rules that specify characteristics of areas that may function as a reentry circuit. The characteristics may be shape (e.g., 3D shape), location, and electrical activity of border zone tissue and scar tissue such as those of FIG. 9. A cardiac cycle (e.g., fibrillation cycle) resulting from a reentrant circuit represents the electrical activity from the exit site to the entrance site and through the isthmus to the exit site. Each simulation may simulate electrical activity over a fixed time or until, for example, a fibrillation stabilizes (i.e., the beat-to-beat consistency of a dominant arrhythmia source localized to a particular region in the heart).

After a simulation completes, the RML system identifies a loop near the scar tissue based on the flow of action potential that loops back to itself during a cycle. The entrance site of the loop can be identified based on analysis of the conduction velocity. The isotropic characteristics of the conduction velocity based on along-fiber and cross-fiber conduction velocities aid in the identification of the entrance site. The RML system identifies the exit site based on analysis of a cardiogram (e.g., a vectorcardiogram (VCG)) generated dynamically from a series of simulated electrical activity represented by calculated values such as action potentials of the vertices of the 3D mesh. When the RML system identifies the start of depolarization near an entrance site, the RML system analyzes the electrical activity to identify the location where the depolarization was initiated. The RML system may generate a probability of being an exit site for multiple locations. The isthmus is the path (e.g., between scar tissue) along the loop from the entrance site to the exit site in the direction of the flow of action potential.

To identify an exit site (and possibly entrance site and isthmus) for a patient, 2D images indicating perfusion, motion, electrical activity, and so on are collected from the patient. The 2D images or a 3D image derived from the 2D images and/or features derived from the 2D images, such as areas of scar tissue, are input to the RML model, which outputs the exit site and possibly the entrance site and/or isthmus. The RML system may then display the reentrant circuit as a 2D graphic (e.g., FIG. 9) or as a 3D graphic similar to the 3D graphic based on a 3D model generated by the TSGD system. To provide the entrance and the isthmus characteristics, a separate model may alternatively be trained to input exit site information and scar tissue information and output a 2D model or a 3D model of the reentrant circuit with the entrance site and the isthmus demarcated.

The RML system may indicate one or more exit sites (and corresponding loops and entrance sites) on a 2D, 3D, or 4D graphic of a heart. The various locations that may be an exit site of a reentrant circuit may be indicated by color intensities that represent the probabilities of each exit site.

The computing systems (e.g., network nodes or collections of network nodes) on which the TSGD system, the RML system, and the other described systems may be implemented may include a central processing unit, input devices, output devices (e.g., display devices and speakers), storage devices (e.g., memory and disk drives), network interfaces, graphics processing units, communications links (e.g., Ethernet, Wi-Fi, cellular, and Bluetooth), global positioning system devices, and so on. The input devices may include keyboards, pointing devices, touch screens, gesture recognition devices (e.g., for air gestures), head and eye tracking devices, microphones for voice recognition, and so on. The computing systems may include high-performance computing systems, cloud-based computing systems, client computing systems that interact with cloud-based computing systems, desktop computers, laptops, tablets, e-readers, personal digital assistants, smartphones, gaming devices, servers, and so on. The computing systems may access computer-readable media that include computer-readable storage media and data transmission media. The computer-readable storage media are tangible storage means that do not include a transitory, propagating signal. Examples of computer-readable storage media include memory such as primary memory, cache memory, and secondary memory (e.g., DVD) and other storage. The computer-readable storage media may have recorded on them or may be encoded with computer-executable instructions or logic that implements the TSGD system, the RML system, and the other described systems. The data transmission media are used for transmitting data via transitory, propagating signals or carrier waves (e.g., electromagnetism) via a wired or wireless connection. The computing systems may include a secure cryptoprocessor as part of a central processing unit for generating and securely storing keys and for encrypting and decrypting data using the keys.

The TSGD system, the RML system, and the other described systems may be described in the general context of computer-executable instructions, such as program modules and components, executed by one or more computers, processors, or other devices. Program modules or components include routines, programs, objects, data structures, and so on that perform tasks or implement data types of the TSGD system, the RML system, and the other described systems. Typically, the functionality of the program modules may be combined or distributed as desired. Aspects of the TSGD system, the RML system, and the other described systems may be implemented in hardware using, for example, an application-specific integrated circuit (ASIC) or a field programmable gate array (FPGA).

A machine learning (ML) model may be any of a variety or combination of supervised or unsupervised machine learning models including a neural network, such as a fully connected, convolutional, recurrent, or autoencoder neural network, or a restricted Boltzmann machine, a support vector machine, a Bayesian classifier, k-means clustering technique, and so on. When the machine learning model is a deep neural network, the training results are a set of weights for the activation functions of the deep neural network. A support vector machine operates by finding a hyper-surface in the space of possible inputs. The hyper-surface attempts to split the positive examples from the negative examples by maximizing the distance between the nearest of the positive and negative examples to the hyper-surface. This step allows for correct classification of data that is similar to but not identical to the training data. A machine learning model may generate values of a discrete domain (e.g., classification), probabilities, and/or values of a continuous domain (e.g., regression value).

Various techniques can be used to train a support vector machine, such as adaptive boosting, which is an iterative process that runs multiple tests on a collection of training data. Adaptive boosting transforms a weak learning algorithm (an algorithm that performs at a level only slightly better than chance) into a strong learning algorithm (an algorithm that displays a low error rate). The weak learning algorithm is run on different subsets of the training data. The algorithm concentrates increasingly on those examples in which its predecessors tended to show mistakes. The algorithm corrects the errors made by earlier weak learners. The algorithm is adaptive because it adjusts to the error rates of its predecessors. Adaptive boosting combines rough and moderately inaccurate rules of thumb to create a high-performance algorithm. Adaptive boosting combines the results of each separately run test into a single accurate classifier. Adaptive boosting may use weak classifiers that are single-split trees with only two leaf nodes.

A neural network model has three major components: an architecture, a cost function, and a search algorithm. The architecture defines the functional form relating the inputs to the outputs (in terms of network topology, unit connectivity, and activation functions). The search in weight space for a set of weights that minimizes the objective function is the training process. In one embodiment, the classification system may use a radial basis function (RBF) network and a standard gradient descent as the search technique.

A convolutional neural network (CNN) has multiple layers such as a convolutional layer, a rectified linear unit (ReLU) layer, a pooling layer, a fully connected (FC) layer, and so on. Some more complex CNNs may have multiple convolutional layers, ReLU layers, pooling layers, and FC layers.

A convolutional layer may include multiple filters (also referred to as kernels or activation functions). A filter inputs a convolutional window, for example, of an image, applies weights to each pixel of the convolutional window, and outputs an activation value for that convolutional window. For example, if the static image is 256 by 256 pixels, the convolutional window may be 8 by 8 pixels. The filter may apply a different weight to each of the 64 pixels in a convolutional window to generate the activation value, also referred to as a feature value. The convolutional layer may include, for each filter, a node (also referred to as a neuron) for each pixel of the image, assuming a stride of one with appropriate padding. Each node outputs a feature value based on a set of weights for the filter that is learned.

The ReLU layer may have a node for each node of the convolutional layer that generates a feature value. The generated feature values form a ReLU feature map. The ReLU layer applies a filter to each feature value of a convolutional feature map to generate feature values for a ReLU feature map. For example, a filter such as max(0, activation value) may be used to ensure that the feature values of the ReLU feature map are not negative.

The pooling layer may be used to reduce the size of the ReLU feature map by downsampling the ReLU feature map to form a pooling feature map. The pooling layer includes a pooling function that inputs a group of feature values of the ReLU feature map and outputs a feature value.

The FC layer includes some number of nodes that are each connected to every feature value of the pooling feature maps.

A generative adversarial network (GAN) or an attribute (attGAN) may also be used. An attGAN employs a GAN to train the generator model. (See Zhenliang He, Wangmeng Zuo, Meina Kan, Shiguang Shan, and Xilin Chen, "AttGAN: Facial Attribute Editing by Only Changing What You Want," IEEE Transactions on Image Processing, 2018; and Ian Goodfellow, Jean Pouget-Abadie, Mehdi Mirza, Bing Xu, David Warde-Farley, Sherjil Ozair, Aaron Courville, and Yoshua Bengio, "Generative Adversarial Nets," Advances in Neural Information Processing Systems, pp. 2672-2680, 2014, which are hereby incorporated by reference.) An attGAN includes a generator, a discriminator, and an attGAN classifier and is trained using training data that includes input images of objects and input attribute values of each object. The generator includes a generator encoder and a generator decoder. The generator encoder inputs an input image and is trained to generate a latent vector of latent variables representing the input image. The generator decoder inputs the latent vector for an input image and the input attribute values. The attGAN classifier inputs an image and generates a prediction of its attribute values. The attGAN is trained to generate a modified image that represents the input image modified based on the attribute values. The generator encoder and the generator decoder form the generator model.

Figure 10:
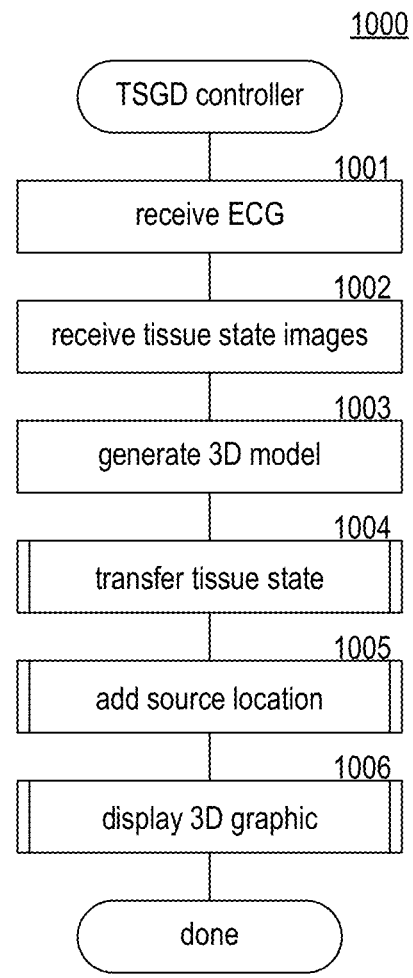
FIG. 10 is a flow diagram that illustrates the overall processing of the TSGD system in some embodiments.

FIG. 10 is a flow diagram that illustrates the overall processing of the TSGD system in some embodiments. A TSGD controller 1000 controls the generation of a 3D model and the display of the 3D model as a 3D graphic with tissue state and source location information. In block 1001, the controller receives an electrogram of electrical activity of an organ. The electrogram may be collected, for example, using a 12-lead electrocardiograph machine. In block 1002, the component receives tissue state images that may be collected using a scanning technology such as a sestamibi scan. In block 1003, the component generates a 3D model representing a patient organ. In block 1004, the component transfers the tissue state from tissue state images to the 3D model to augment the 3D model. In block 1005, the component adds source location information to the 3D model. In block 1006, the component displays a 3D graphic based on the 3D model that illustrates the tissue state and the source location of the organ. The component then completes.

Figure 11:
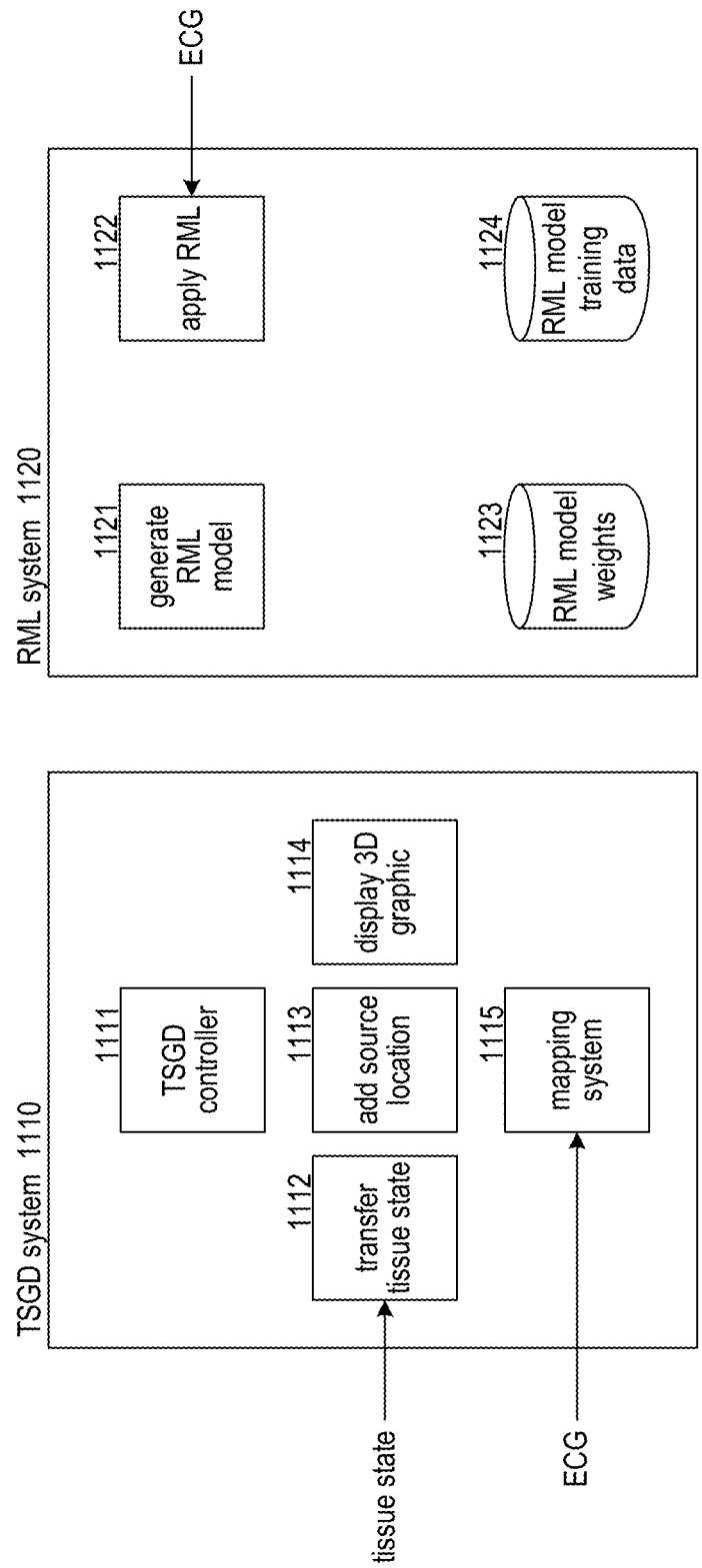
FIG. 11 is a block diagram that illustrates components of the TSGD system and the RML system in some embodiments.

FIG. 11 is a block diagram that illustrates components of the TSGD system and the RML system in some embodiments. The TSGD system 1110 includes a TSGD controller 1111, a transfer tissue state component 1112, an add source location component 1113, a display 3D graphic component 1114, and a mapping system 1115. As described above, the TSGD controller controls the overall processing of the TSGD system. The transfer tissue state component receives 2D images indicating tissue state and transfers the tissue state to a 3D model. The add source location component receives an electrocardiogram, accesses the mapping system to identify source location information, and adds the source location information to the 3D model to augment the 3D model. The display 3D graphic component generates a 3D graphic from the 3D model with the tissue state and source location information and controls the display of the 3D graphic.

The RML system 1120 includes a generate RML model component 1121, an apply RML model component 1122, an RML model weights data store 1123, and an RML model training data store 1124. The generate RML model component generates an RML model using the training data and stores the learned RML model weights in the RML model weights data store. The apply RML model component inputs exit site and scar tissue information and applies the RML model, using the RML model weights, to the exit site and scar tissue to determine a corresponding entrance site and isthmus. Various components of the TSGD system and the RML system may be provided by different computing systems. For example, the mapping system may be implemented on cloud-based computing systems, and the display 3D graphic component may be implemented on a client computing system. When implemented on different computing systems, the computing systems may send data to and receive data from each other. For example, a client computing system may send an electrogram such as a cardiogram (e.g., electrocardiogram (ECG) or vectorcardiogram (VCG)), an electrogastrogram (EGG), or an electroencephalogram (EEG), to a cloud-based mapping system and receive source location information from the cloud-based mapping component.

Figure 12:
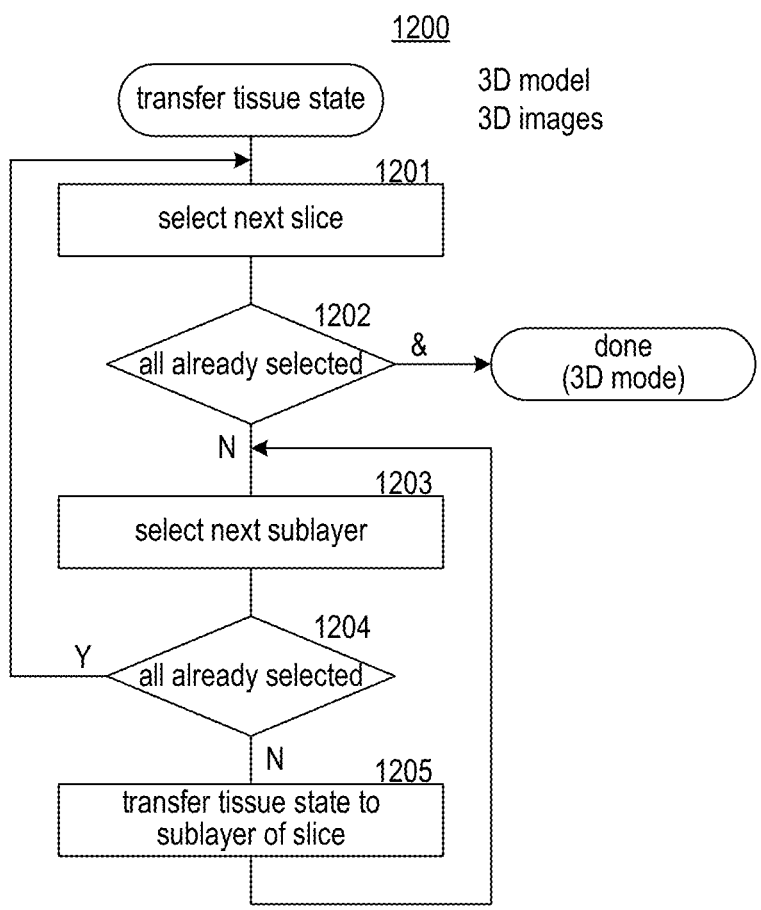
FIG. 12 is a flow diagram that illustrates the processing of a transfer tissue state component of the TSGD system in some embodiments.

FIG. 12 is a flow diagram that illustrates the processing of a transfer tissue state component of the TSGD system in some embodiments. The transfer tissue state component 1200 inputs a 3D model and 2D images that indicate the tissue state and transfers the tissue state to the 3D model. In block 1201, the component selects the next slice of the 2D images and the corresponding 3D model slice of the 3D model. In decision block 1202, if all the slices have already been selected, then the component completes, else the component continues at block 1203. In block 1203, the component selects the next sublayer of the selected slice. In decision block 1204, if all the sublayers have already been selected, then the component loops to block 1201 to select the next sublayer of the selected slice, else the component continues at block 1205. In block 1205, the component transfers the tissue state to the selected sublayer of the selected slice of the 3D model and then loops to block 1203 to select the next sublayer.

Figure 13:
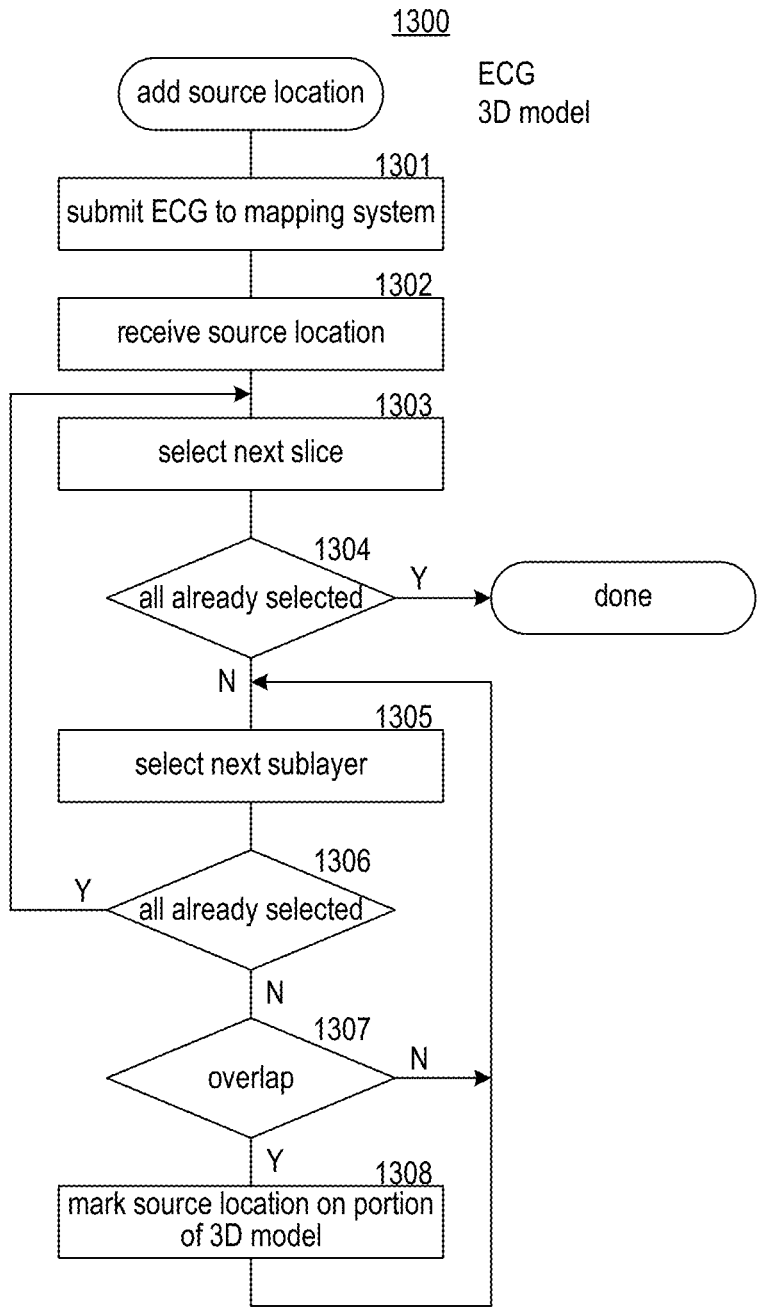
FIG. 13 is a flow diagram that illustrates the processing of an add source location component of the TSGD system in some embodiments.

FIG. 13 is a flow diagram that illustrates the processing of an add source location component of the TSGD system in some embodiments. The add source location component is invoked, passing an indication of an ECG and a 3D model, and transfers the source location information to the 3D model. In block 1301, the component submits the ECG to a mapping system to identify source location information. In block 1302, the component receives the source location information. In block 1303, the component selects a slice of the 3D model. In decision block 1304, if all the slices have already been selected, then the component completes, else the component continues at block 1305. In block 1305, the component selects the next sublayer of the selected slice. In decision block 1306, if all the sublayers have already been selected, then the component loops to block 1303 to select the next slice, else the component continues at block 1307. In decision block 1307, if the source location information overlaps with the selected sublayer within the selected slice, the component continues at block 1308, else the component loops to block 1305 to select the next sublayer. In block 1308, the component marks the source location information on the portion of the 3D model represented by the selected slice and selected sublayer.

Figure 14:
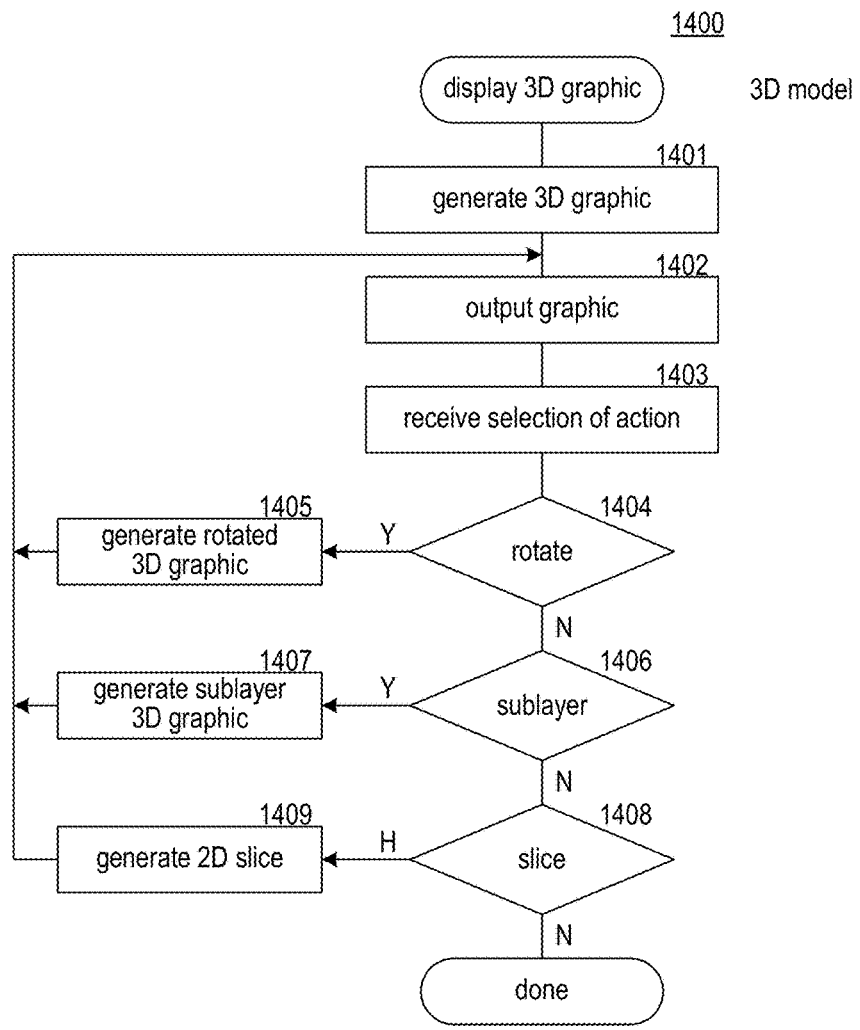
FIG. 14 is a flow diagram that illustrates the processing of a display 3D graphic component of the TSGD system in some embodiments.

FIG. 14 is a flow diagram that illustrates the processing of a display 3D graphic component of the TSG system in some embodiments. The display 3D graphic component 1400 is passed a 3D model and controls the display of a 3D graphic generated from the 3D model. In block 1401, the component generates a 3D graphic based on the 3D model. In block 1402, the component outputs a graphic such as the 3D graphic or 2D slices. In block 1403, the component receives a selection of an action, which may be to terminate the display of the 3D graphic, rotate the 3D graphic, display a certain sublayer, and display a certain slice. In decision block 1404, if the action is to rotate the 3D graphic, then the component continues at block 1405 to generate the rotated 3D graphic, else the component continues at block 1406. In block 1406, if the action is to display a certain sublayer, then the component continues at block 1407 to generate a 3D graphic based on that sublayer, else the component continues at block 1408. In decision block 1408, if the action is to display a certain slice, then the component continues at block 1409 to generate a 2D slice from the 3D model, else the component completes. After performing the processing of blocks 1405, 1407, and 1409, the component loops to block 1402 to output the graphic.

Figure 15:
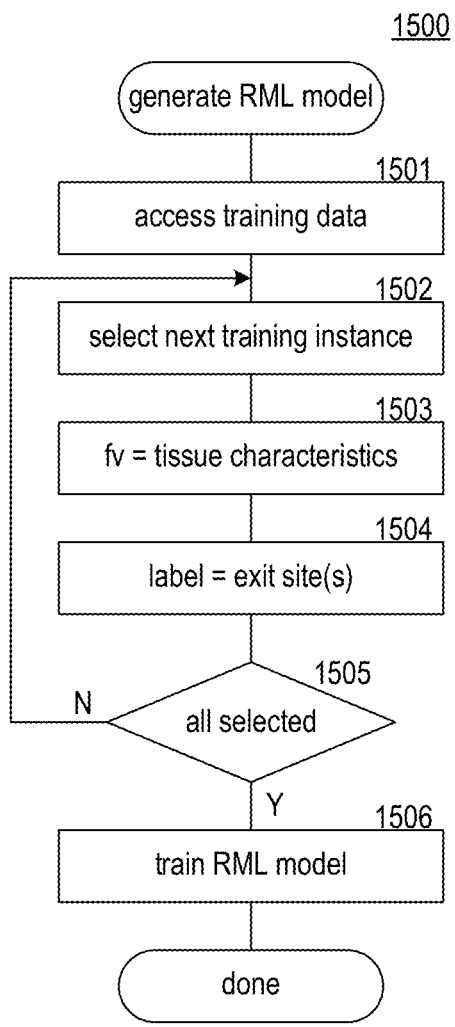
FIG. 15 is a flow diagram that illustrates the processing of a generate RML model of the RML system in some embodiments.

FIG. 15 is a flow diagram that illustrates the processing of a generate RML model of the RML system in some embodiments. The generate RML model component 1500 trains an RML model based on the training data of the RML model training data store. The training data includes training instances that may specify a reentrant circuit or non-reentrant scar tissue along with an indication of an exit site for a reentrant circuit or an indication of no exit site for non-reentrant scar tissue. Alternatively, the training data may have only training instances for reentrant circuits. When both reentrant scar tissue and non-reentrant scar tissue are used, one ML model may be trained to distinguish a reentrant circuit from non-reentrant scar tissue, and another ML model may be trained to indicate an exit site for a reentrant circuit. Also, a separate ML model may be trained to identify an entrance site and an isthmus given tissue characteristics and an exit site of a reentrant circuit. Each RML model is trained with training data that includes the output data to be identified as a label and the input data that is used to identify the output data as a feature vector. In block 1501, the component accesses the RML model training data. In block 1502, the component selects the next training instance of the RML training data. In block 1503, the component generates a feature vector that includes tissue characteristics (e.g., perfusion or electrical characteristics) within a 3D model of the training instance. In block 1504, the component labels the feature vector with the exit site location and possibly entrance site location and isthmus information of the training instance. In decision block 1505, if all the training instances have been selected, then the component continues at block 1506, else the component loops to block 1502 to select the next training instance. In block 1506, the component trains the RML model using the labeled feature vectors and stores the learned weights in the RML model weights data store and then completes.

The following paragraphs describe various aspects of the TSGD system and the RML system. An implementation of the system may employ any combination of the aspects. The processing described below may be performed by a computing system with a processor that executes computer-executable instructions stored on a computer-readable storage medium that implements the system.

In some aspects, the techniques described herein relate to a method performed by one or more computing systems for augmenting a three-dimensional (3D) model of a heart to indicate tissue state, the method including: accessing a 3D model of a heart; accessing two-dimensional (2D) images of tissue state slices of the heart, the tissue state slices having tissue state information of the heart; accessing source location information of an arrhythmia; augmenting the 3D model with an indication of a source location based on the source location information; for each of a plurality of the tissue state slices of the heart, augmenting a 3D model slice of the 3D model that corresponds to that tissue state slice with an indication of the tissue state of the heart represented by the tissue state information of that tissue state slice; and displaying a representation of the 3D model that indicates the source location of the arrhythmia and the tissue state of the heart. In some aspects, the techniques described herein relate to a method wherein the representation of the 3D model that is displayed is a 3D graphic. In some aspects, the techniques described herein relate to a method wherein the representation of the 3D model is a 3D model slice of the 3D model. In some aspects, the techniques described herein relate to a method wherein the 3D model includes a plurality of 3D model sublayers of a layer of a heart wall of the 3D model, wherein the augmenting of the 3D model augments a plurality of 3D model sublayers with an indication of the source location as represented by the source location information, and wherein the augmenting of a 3D model slice augments a plurality of 3D model sublayers with an indication of the tissue state as represented by the tissue state information. In some aspects, the techniques described herein relate to a method wherein the layer is an endocardium, a myocardium, or an epicardium of a heart wall. In some aspects, the techniques described herein relate to a method further including receiving a selection of a 3D model sublayer and wherein the representation of the 3D model is a 3D graphic that indicates the source location and the tissue state of the selected 3D model sublayer. In some aspects, the techniques described herein relate to a method wherein the augmenting of a 3D model sublayer is performed dynamically as the sublayer is selected. In some aspects, the techniques described herein relate to a method wherein the 2D images are derived from a sestamibi scan of the heart. In some aspects, the techniques described herein relate to a method wherein the 2D images are derived from a positron emission tomography scan of the heart. In some aspects, the techniques described herein relate to a method wherein the 2D images are derived from an echocardiography scan of the heart. In some aspects, the techniques described herein relate to a method wherein the 2D images are derived from a computed tomography scan of the heart. In some aspects, the techniques described herein relate to a method wherein the 2D images are derived from a voltage map of the heart. In some aspects, the techniques described herein relate to a method wherein the 2D images are derived from a magnetic resonance imaging scan of the heart. In some aspects, the techniques described herein relate to a method wherein the 2D images are slices of a 3D image of a scan of the heart. In some aspects, the techniques described herein relate to a method wherein the tissue state of 2D slices is based on a scan indicating cardiac perfusion within the heart. In some aspects, the techniques described herein relate to a method wherein the tissue state of 2D slices is based on a scan indicating motion of a heart wall of the heart. In some aspects, the techniques described herein relate to a method wherein the tissue state indicates normal tissue, border zone tissue, and scar tissue. In some aspects, the techniques described herein relate to a method wherein the tissue state is based on electrical, metabolic, and/or perfusion activity of the heart. In some aspects, the techniques described herein relate to a method further including, for each of a plurality of 3D models of a four-dimensional (4D) model of the heart, augmenting that 3D model to indicate source location and tissue state of the heart. In some aspects, the techniques described herein relate to a method wherein the 4D model represents movement of a heart wall of the heart. In some aspects, the techniques described herein relate to a method wherein the accessing of the source location information includes accessing a cardiogram and identifying source location information based on mappings that each map a cardiogram to source location information. In some aspects, the techniques described herein relate to a method wherein the 3D model is generated from 2D images of the heart based on mappings that each map 2D images to a 3D image. In some aspects, the techniques described herein relate to a method wherein the 3D model is generated based on an anatomical mapping of the heart. In some aspects, the techniques described herein relate to a method wherein the 3D model is generated based on a scan of the heart. In some aspects, the techniques described herein relate to a method further including displaying a 3D model slice graphic that includes an indication of the source location and the tissue state of that 3D model slice. In some aspects, the techniques described herein relate to a method wherein the augmenting of the 3D model indicates different tissue states using different colors.

In some aspects, the techniques described herein relate to one or more computing systems for augmenting a three-dimensional (3D) model of an organ to indicate tissue state of an organ, the one or more computing systems including: one or more computer-readable storage mediums that store: a model of the organ, the model including an indication of a source location relating to an abnormality of the organ; a tissue state representation of tissue state of the organ that is based on a scan of the organ; and computer-executable instructions for controlling the one or more computing systems to: augment the model with the tissue state of the organ based on the tissue state representation; and output a representation of the model that indicates the source location and the tissue state of the organ; and one or more processors for controlling the one or more computing systems to execute the one or more computer-executable instructions. In some aspects, the techniques described herein relate to one or more computing systems wherein a first computing system stores the instructions to augment and a second computing system stores the instructions to output. In some aspects, the techniques described herein relate to one or more computing systems wherein the first computing system includes instructions to receive the tissue state representation, provide the tissue state representation to the second computing system, receive the output representation from the second computing system, and display the output representation. In some aspects, the techniques described herein relate to one or more computing systems wherein the second computing system is a cloud-based system. In some aspects, the techniques described herein relate to one or more computing systems wherein the organ is selected from the group consisting of a heart, a brain, a digestive organ, a lung, a liver, a kidney, a stomach, and a muscle. In some aspects, the techniques described herein relate to one or more computing systems wherein the scan is a noninvasive scan.

In some aspects, the techniques described herein relate to one or more computing systems for generating a reentry machine learning (RML) model for identifying characteristics of a reentrant circuit of a heart, the one or more computing systems including: one or more computer-readable storage mediums that store computer-executable instructions for controlling the one or more computing systems to: access training data that includes descriptions of characteristics of reentrant circuits; for each description, extracting one or more features from the description; extracting one or more labels from the description; labeling the one or more features with the one or more labels; and training the RML model using the labeled features; and one or more processors for controlling the one or more computing systems to execute the one or more computer-executable instructions. In some aspects, the techniques described herein relate to one or more computing systems wherein the one or more features include tissue state information of a reentrant circuit and the one or more labels include an exit site. In some aspects, the techniques described herein relate to one or more computing systems wherein a feature is an image of an area of scar tissue. In some aspects, the techniques described herein relate to one or more computing systems for identifying an exit site of a reentrant circuit of a heart, the one or more computing systems including: one or more computer-readable storage mediums that store computer-executable instructions for controlling the one or more computing systems to: access subject scar tissue characteristics of a reentrant circuit of a subject; access a reentry machine learning (RML) model for identifying an exit site of the reentrant circuit, the RML model being trained using training data that includes, for each of a plurality of reentrant circuits, information relating to scar tissue of that reentrant circuit that is labeled with information relating to an exit site of that reentrant circuit; apply the RML model to the subject scar tissue characteristics to identify subject information relating to an exit site for the reentrant circuit; and output an indication of the identified subject information; and one or more processors for controlling the one or more computing systems to execute the one or more computer-executable instructions.

Although the subject matter has been described in language specific to structural features and/or acts, it is to be understood that the subject matter defined in the appended claims is not necessarily limited to the specific features or acts described above. Rather, the specific features and acts described above are disclosed as example forms of implementing the claims.

We claim:

1. One or more computing systems for generating a reentry machine learning (RML) model for identifying characteristics of a reentrant circuit of a heart, the one or more computing systems comprising:
   one or more computer-readable storage mediums that store computer-executable instructions for controlling the one or more computing systems to:
      access training data that includes descriptions of characteristics of reentrant circuits,
         the characteristics including a specification of a common pathway from an entrance site to an exit site, and including tissue characteristics that include one or more of perfusion, electrical, and motion characteristics, and
         the training data generated by, for each of a plurality of simulated tissue characteristics, running a simulation of electrical activity of a heart having those simulated tissue characteristics and identifying from the simulated electrical activity a simulated reentrant circuit, each simulated reentrant circuit having a simulated entrance site, simulated exit site, and a simulated common pathway;
      for each description of characteristics of a reentrant circuit,
         extracting one or more features from the description that include a tissue characteristic;
         extracting one or more labels from the description that include a specification of the common pathway of the description; and
         labeling the one or more features with the one or more labels; and
      training the RML model using the labeled features; and
   one or more processors for controlling the one or more computing systems to execute the computer-executable instructions.

2. The one or more computing systems of claim 1 wherein the one or more features include tissue state information of a reentrant circuit and the one or more labels include an exit site.

3. The one or more computing systems of claim 1 wherein a feature is an image of an area of scar tissue.

4. The one or more computing systems of claim 1 wherein the computer-executable instructions further control the one or more computing systems to, for each simulated tissue characteristics:
   run a simulation of electric activity of a heart based on those simulated tissue characteristics;
   identify a loop in conduction velocity near scar tissue during a simulated cycle;
   identify a simulated entrance site and simulated exit site within the identified loop; and
   identify a simulated common pathway based on direction of flow of action potential represented by the simulated electrical activity from the simulated entrance site to the simulated exit site.

5. The one or more computing systems of claim 4 wherein the computer-executable instructions further control the one or more computing systems to:
   generate a simulated cardiogram based on the simulated electrical activity of the simulated cycle;
   identify the simulated exit site based on analysis of the simulated cardiogram; and
   identify the simulated entrance site based on isotropic characteristics of conduction velocity.

6. The one or more computing systems of claim 4 wherein the computer-executable instructions further control the one or more computing systems to:
   identify a simulated loop in flow of simulated action potential as indicated by the simulated electrical activity; and
   identify the simulated entrance site based on isotropic characteristics of simulated conduction velocity.

7. The one or more computing systems of claim 1 wherein the tissue characteristics include indications of normal tissue, scar tissue and border zone tissue.

8. The one or more computing systems of claim 1 wherein the computer-executable instructions further control the one or more computing systems to:

access a patient characteristics that include and one or more of perfusion, electrical, and motion characteristics; and apply the trained RML model to the patient characteristics to identify a specification of a patient common pathway of a patient reentrant circuit.

9. The one or more computing systems of claim 8 wherein the computer-executable instructions further control the one or more computing systems to display a three-dimensional (3D) graphic of heart that includes an indication of the patient reentrant circuit.

10. One or more computing systems for identifying an entrance site, a common pathway, and an exit site of a reentrant circuit of a heart, the one or more computing systems comprising:

one or more computer-readable storage mediums that store computer-executable instructions for controlling the one or more computing systems to:
access subject tissue characteristics of a subject reentrant circuit of a subject, the subject tissue characteristics includes a specification of scar tissue and border zone tissue;
access a reentry machine learning (RML) model for identifying an entrance site, a common pathway, and an exit site of the reentrant circuit, the RML model being trained using training data that includes, for each of a plurality of simulated reentrant circuits, information relating to simulated scar tissue and simulated border zone tissue of that simulated reentrant circuit that is labeled with information relating to a simulated entrance site, a simulated common pathway, and a simulated exit site of that simulated reentrant circuit;
apply the RML model to the subject tissue characteristics to identify subject information relating to an entrance site, a common pathway, and an exit site for the subject reentrant circuit; and
output an indication of the identified subject information; and
one or more processors for controlling the one or more computing systems to execute the computer-executable instructions.

11. The one or more computing systems of claim 10 wherein the computer-executable instructions further control the one or more computing systems to, for each of a plurality of simulated tissue characteristics:
run a simulation of electric activity of a heart based on those simulated tissue characteristics;
identify a loop in conduction velocity during a cycle;
generate a simulated cardiogram based on the simulated electrical activity of the cycle;
identify a simulated exit site based on analysis of the simulated cardiogram;
identify a simulated entrance site based on isotropic characteristics of conduction velocity; and
identify a simulated common pathway based on direction of flow of action potential represented by the simulated electrical activity from the simulated entrance site to the simulated exit site.

12. The one or more computing systems of claim 11 wherein the simulated tissue characteristics include indications of normal tissue, scar tissue and border zone tissue.

13. The one or more computing systems of claim 11 wherein the computer-executable instructions further control the one or more computing systems to display a three-dimensional (3D) graphic of heart that includes an indication of the subject reentrant circuit.

14. A method performed by one or more computing systems for simulating electrical activity of a reentrant circuit of a heart, the method comprising:
generating a plurality of sets of simulation parameters that each specify areas of normal tissue, scar tissue, and border zone tissue; and
for each set of simulation parameters,
simulating electrical activity of a heart having areas of scar tissue and border zone tissue as specified by the set of simulation parameters; and
when a simulated arrhythmia has stabilized,
generating a simulated cardiogram based on the simulated electrical activity during a simulated cardiac cycle;
analyzing the simulated electrical activity to identify a loop near scar tissue based on flow of simulated action potential that loops back to itself during the simulated cardiac cycle;
identifying an entrance site of the loop based on simulated conduction velocity;
identifying an exit site of the loop based on the simulated cardiogram; and
storing a mapping of one or more of the simulation parameters to one or more of the identified entrance site, the identified loop, and the identified exit site.

15. The method of claim 14 further comprising identifying a common pathway based on the identified entrance site, the identified loop, and the identified exit site.

16. The method of claim 14 wherein a plurality of the areas of scar tissue and border zone tissue are derived from images collected from patients.

17. The method of claim 14 wherein a plurality of the areas of scar tissue and border zone tissue are generated based on rules that specify characteristics of areas that may function as a reentrant circuit.

18. The method of claim 14 wherein the simulating is run until an arrhythmia has stabilized.

19. The method of claim 14 wherein the identifying of the exit site applies a machine learning model to the simulated cardiogram to identify the exit site.

20. The method of claim 14 further comprising training a reentrant machine learning model using feature vectors with a feature derived from images of reentrant circuits and each feature vector having a label based on an entrance site, a common pathway, and an exit site identified based on a simulation that is based on scar tissue and border zone tissue derived from an image.

21. The method of claim 14 further comprising training a reentrant machine learning model using feature vectors with features derived from a specification of scar tissue and border zone tissue of reentrant circuits and each feature vector having a label based on one or more of an entrance site, a common pathway, and an exit site identified based on a simulation that is based on the specification of scar tissue and border zone tissue.

22. A method performed by one or more computing systems for identifying a reentrant circuit characteristic of a reentrant circuit of a heart, the method comprising:
accessing a subject image of a subject reentrant circuit of a subject;
accessing a reentry machine learning (RML) model for identifying a reentrant circuit characteristic based on tissue characteristics relating to scar tissue and border zone tissue identified from the subject image, the RML model being trained using training data that includes, for each of a plurality of simulated reentrant circuits, simulated tissue characteristics relating to simulated scar tissue and simulated border zone tissue of that simulated reentrant circuit that is labeled with a simulated reentrant circuit characteristic of that simulated reentrant circuit;

applying the RML model to subject tissue characteristics of the subject to identify a subject reentrant circuit characteristic for the subject reentrant circuit; and outputting an indication of the identified subject reentrant circuit characteristic.

23. The method of claim 22 wherein outputting outputs a three-dimensional (3D) graphic of a heart the identified subject reentrant circuit indicates.

24. The method of claim 22 further comprising, for each of a plurality of specifications of normal tissue, border zone tissue, and scar tissue of a heart:

simulating electrical activity of that heart based on that specification, the simulated electrical activity including simulated action potential and simulated conduction velocity; and when a simulated arrhythmia has stabilized,
generating a simulated cardiogram based on the simulated electrical activity during a simulated cardiac cycle;

analyzing the simulated electrical activity to identify a loop near scar tissue based on flow of simulated action potential that loops back to itself during the simulated cardiac cycle;

identifying an entrance site of the loop based on simulated conduction velocity;

identifying an exit site of the loop based on the simulated cardiogram; and storing a mapping of the specification to one or more of the identified entrance site, the identified loop, and the identified exit site.

* * * * *